US00RE47375E

(19) United States
(12) Reissued Patent
Shields et al.

(10) Patent Number: US RE47,375 E
(45) Date of Reissued Patent: May 7, 2019

(54) TISSUE SEALER WITH NON-CONDUCTIVE VARIABLE STOP MEMBERS AND METHOD OF SEALING TISSUE

(71) Applicant: Covidien AG, Neuhausen am Rheinfall (CH)

(72) Inventors: Chelsea Shields, San Francisco, CA (US); Edward C Meagher, Greenlawn, NY (US)

(73) Assignee: Coviden AG, Neuhausen am Rheinfall (CH)

(21) Appl. No.: 14/813,325

(22) Filed: Jul. 30, 2015

Related U.S. Patent Documents

Reissue of:

(64) Patent No.: 8,496,656
Issued: Jul. 30, 2013
Appl. No.: 12/355,622
Filed: Jan. 16, 2009

U.S. Applications:

(63) Continuation of application No. 10/846,262, filed on May 14, 2004, now Pat. No. 7,491,201.

(Continued)

(51) Int. Cl.

| | |
|---|---|
| ***A61B 18/14*** | (2006.01) |
| ***A61B 17/22*** | (2006.01) |
| *A61B 17/28* | (2006.01) |

(52) U.S. Cl.

CPC ..... *A61B 17/22031* (2013.01); *A61B 17/28* (2013.01)

(58) Field of Classification Search

CPC ..... A61B 18/1445; A61B 18/1442; A61B 17/22031; A61B 17/18

(Continued)

(56) References Cited

U.S. PATENT DOCUMENTS

| | | | |
|---|---|---|---|
| 1,586,645 | A | 6/1926 | Bierman |
| 1,813,902 | A | 7/1931 | Bovie |

(Continued)

FOREIGN PATENT DOCUMENTS

| | | |
|---|---|---|
| CA | 2104423 | 2/1994 |
| CA | 2104423 A1 | 2/1994 |

(Continued)

OTHER PUBLICATIONS

US 6,663,629, 12/2003, Buysse et al. (withdrawn)

(Continued)

*Primary Examiner* — Beverly M Flanagan

(57) ABSTRACT

[A bipolar forceps for sealing tissue includes an elongated shaft having opposing jaw members at a distal end thereof, each of the jaw members including an electrically conductive sealing surface. The jaw members are movable relative to one another from a first position wherein the jaw members are disposed in spaced relation relative to one another to a second position wherein the jaw members cooperate to grasp tissue therebetween. The bipolar forceps is connected to a source of electrical energy such that the jaw members are capable of conducting bipolar energy through tissue grasped therebetween to effect a seal. The distance between the electrically conductive sealing surfaces when tissue is held therebetween is adjusted based upon a sensed pre-surgical condition during activation.] *A bipolar forceps for sealing tissue includes an elongated shaft having opposing jaw members at a distal end thereof, each of the jaw members including an electrically conductive sealing surface. The jaw members are movable relative to one another from a first*

(Continued)

*position wherein the jaw members are disposed in spaced relation relative to one another to a second position wherein the jaw members cooperate to grasp tissue therebetween. The bipolar forceps is connected to a source of electrical energy such that the jaw members are capable of conducting bipolar energy through tissue grasped therebetween to affect a seal. The distance between the electrically conductive sealing surfaces when tissue is held therebetween is adjusted based upon a sensed pre-surgical condition during activation.*

10 Claims, 5 Drawing Sheets

Related U.S. Application Data

(60) Provisional application No. 60/470,632, filed on May 15, 2003.

(58) Field of Classification Search
USPC ..... 606/45–52; 294/99.2
See application file for complete search history.

(56) References Cited

U.S. PATENT DOCUMENTS 1,822,330 A 9/1931 Ainslie
1,852,542 A 4/1932 Sovatkin
2,002,594 A 5/1935 Wappler et al.
2,011,169 A 8/1935 Wappler
2,031,682 A 2/1936 Wappler et al.
2,054,149 A 9/1936 Wappler
2,176,479 A 10/1939 Willis
2,305,156 A 4/1941 Grubel
2,279,753 A 4/1942 Knopp
2,327,353 A 8/1943 Karle
2,632,661 A 8/1948 Cristofv
2,668,538 A 2/1954 Baker
2,796,065 A 6/1957 Kapp
3,073,311 A 1/1963 Tibbs et al.
3,459,187 A 3/1967 Pallotta
3,372,288 A 3/1968 Wigington
3,643,663 A 2/1972 Sutter
3,648,001 A 3/1972 Anderson et al.
3,651,811 A 3/1972 Hildebrandt et al.
3,678,229 A 7/1972 Osika
3,720,896 A 3/1973 Beierlein
3,763,726 A 10/1973 Hildebrand
3,779,918 A 12/1973 Ikeda et al.
3,801,766 A 4/1974 Morrison, Jr.
3,862,630 A 1/1975 Balamuth
3,863,339 A 2/1975 Reaney et al.
3,866,610 A 2/1975 Kletschka
3,911,766 A 10/1975 Fridolph et al.
3,920,021 A 11/1975 Hiltebrandt
3,921,641 A 11/1975 Hulka
3,938,527 A 2/1976 Rioux et al.
3,952,749 A 4/1976 Fridolph et al.
3,970,088 A 7/1976 Morrison
3,987,795 A 10/1976 Morrison
4,005,714 A 2/1977 Hiltebrandt
4,016,881 A 4/1977 Rioux et al.
4,041,952 A 8/1977 Morrison, Jr. et al.
4,043,342 A 8/1977 Morrison, Jr.
4,074,718 A 2/1978 Morrison, Jr.
4,076,028 A 2/1978 Simmons
4,080,820 A 3/1978 Allen
4,088,134 A 5/1978 Mazzariello
4,112,950 A 9/1978 Pike
4,127,222 A 11/1978 Adams
4,128,099 A 12/1978 Bauer
4,165,746 A 8/1979 Burgin
4,187,420 A 2/1980 Piber
4,233,734 A 11/1980 Bies
4,236,470 A 12/1980 Stenson
4,300,564 A 11/1981 Furihata
4,311,145 A 1/1982 Esty et al.
D263,020 S 2/1982 Rau, III
4,370,980 A 2/1983 Lottick
4,375,218 A * 3/1983 DiGeronimo ..... 606/52
4,416,276 A 11/1983 Newton et al.
4,418,692 A 12/1983 Guay
4,443,935 A 4/1984 Zamba et al.
4,452,246 A 6/1984 Bader et al.
4,470,786 A 9/1984 Sano et al.
4,492,231 A 1/1985 Auth
4,493,320 A 1/1985 Treat
4,503,855 A 3/1985 Maslanka
4,506,669 A 3/1985 Blake, III
4,509,518 A 4/1985 McGarry et al.
4,552,143 A 11/1985 Lottick
4,574,804 A 3/1986 Kurwa
4,597,379 A 7/1986 Kihn et al.
4,600,007 A 7/1986 Lahodny et al.
4,624,254 A 11/1986 McGarry et al.
4,655,215 A 4/1987 Pike
4,655,216 A 4/1987 Tischer
4,657,016 A 4/1987 Garito et al.
4,662,372 A 5/1987 Sharkany et al.
4,671,274 A 6/1987 Sorochenko
4,685,459 A 8/1987 Xoch et al.
371,664 A 10/1987 Brannan et al.
4,733,662 A 3/1988 DeSatnick et al.
D295,893 S 5/1988 Sharkany et al.
D295,894 S 5/1988 Sharkany et al.
4,754,892 A 7/1988 Retief
4,763,669 A 8/1988 Jaeger
4,827,929 A 5/1989 Hodge
4,829,313 A 5/1989 Taggart
4,846,171 A 7/1989 Kauphusman et al.
4,887,612 A 12/1989 Esser et al.
4,938,761 A 7/1990 Ensslin
4,947,009 A 8/1990 Osika et al.
4,985,030 A 1/1991 Melzer et al.
5,007,908 A 4/1991 Rydell
5,026,370 A 6/1991 Lottick
5,026,371 A 6/1991 Rydell et al.
5,035,695 A 7/1991 Weber, Jr. et al.
5,037,433 A 8/1991 Wilk et al.
5,042,707 A 8/1991 Taheri
5,047,046 A 9/1991 Bodoia
5,078,716 A 1/1992 Doll
5,084,057 A 1/1992 Green et al.
5,085,659 A 2/1992 Rydell
5,099,840 A 3/1992 Goble et al.
5,100,430 A 3/1992 Avellanet et al.
5,108,392 A 4/1992 Spingler
5,112,343 A 5/1992 Thornton
5,116,332 A 5/1992 Lottick
5,147,357 A 9/1992 Rose et al.
5,151,102 A 9/1992 Kamiyama et al.
5,151,978 A 9/1992 Bronikowski et al.
5,176,695 A 1/1993 Dulebohn
5,190,541 A 3/1993 Abele et al.
5,196,009 A 3/1993 Kirwan, Jr.
5,197,964 A 3/1993 Parins
5,209,747 A 5/1993 Knoepfler
5,211,655 A 5/1993 Hasson
5,215,101 A 6/1993 Jacobs et al.
5,217,457 A 6/1993 Delahuerga et al.
5,217,458 A 6/1993 Parins
5,217,460 A 6/1993 Knoepfler
5,219,354 A 6/1993 Choudhury et al.
5,244,462 A 9/1993 Delahuerga et al.
5,250,047 A 10/1993 Rydell
5,250,063 A 10/1993 Abidin et al.
5,258,001 A 11/1993 Corman
5,258,006 A 11/1993 Rydell et al.
5,261,918 A 11/1993 Phillips et al.
5,275,615 A 1/1994 Rose
5,277,201 A 1/1994 Stern
5,282,799 A 2/1994 Rydell
5,282,800 A 2/1994 Foshee et al.

(56) References Cited

U.S. PATENT DOCUMENTS 5,282,826 A 2/1994 Quadri
5,290,286 A 3/1994 Parins
5,300,082 A 4/1994 Sharpe et al.
5,304,203 A 4/1994 El-Mallawany et al.
5,308,353 A 5/1994 Beurrier
5,308,357 A 5/1994 Lichtman
5,313,027 A 5/1994 Inoue et al.
5,314,445 A 5/1994 Degwitz et al.
5,318,589 A 6/1994 Lichtman
5,324,289 A 6/1994 Eggers
D348,930 S 7/1994 Olson
5,326,806 A 7/1994 Yokoshima et al.
5,330,471 A 7/1994 Eggers
5,330,502 A 7/1994 Hassler et al.
5,334,183 A 8/1994 Wuchinich
5,334,215 A 8/1994 Chen
5,336,220 A 8/1994 Ryan et al.
5,336,221 A 8/1994 Anderson
5,342,359 A 8/1994 Rydell
5,342,381 A 8/1994 Tidemand
5,342,393 A 8/1994 Stack
5,344,424 A 9/1994 Roberts et al.
5,350,391 A 9/1994 Iacovelli
5,352,222 A 10/1994 Rydell
5,354,271 A 10/1994 Voda
5,356,408 A 10/1994 Rydell
5,366,477 A 11/1994 LeMarie, III et al.
5,368,600 A 11/1994 Failla et al.
5,374,277 A 12/1994 Hassler
5,376,089 A 12/1994 Smith
5,383,875 A 1/1995 Bays et al.
5,383,897 A 1/1995 Wholey
5,389,098 A 2/1995 Tsuruta et al.
5,389,103 A 2/1995 Melzer et al.
5,389,104 A 2/1995 Hahnen et al.
5,391,166 A 2/1995 Eggers
5,391,183 A 2/1995 Janzen et al.
5,396,900 A 3/1995 Slater et al.
5,403,312 A 4/1995 Yates et al.
5,403,342 A 4/1995 Tovey et al.
5,405,344 A 4/1995 Williamson et al.
5,409,763 A 4/1995 Serizawa et al.
5,411,519 A 5/1995 Tovey et al.
5,411,520 A 5/1995 Nash et al.
5,413,571 A 5/1995 Katsaros et al.
5,415,656 A 5/1995 Tihon et al.
5,415,657 A 5/1995 Taymor-Luria
5,422,567 A 6/1995 Matsunaga
5,423,810 A 6/1995 Goble et al.
5,425,690 A 6/1995 Chang
5,425,739 A 6/1995 Jessen
5,429,616 A 7/1995 Schaffer
5,431,672 A 7/1995 Cote et al.
5,431,674 A 7/1995 Basile et al.
5,437,292 A 8/1995 Kipshidze et al.
5,438,302 A 8/1995 Goble
5,439,478 A 8/1995 Palmer
5,441,517 A 8/1995 Kensey et al.
5,443,463 A 8/1995 Stern et al.
5,443,464 A 8/1995 Russell et al.
5,443,480 A 8/1995 Jacobs et al.
5,445,638 A 8/1995 Rydell et al.
5,445,658 A 8/1995 Durrfeld et al.
5,449,480 A 9/1995 Kuriya et al.
5,451,224 A 9/1995 Goble et al.
5,454,823 A 10/1995 Richardson et al.
5,454,827 A 10/1995 Aust et al.
5,456,684 A 10/1995 Schmidt et al.
5,458,598 A 10/1995 Feinberg et al.
5,460,629 A 10/1995 Shlain et al.
5,461,765 A 10/1995 Linden et al.
5,462,546 A 10/1995 Rydell
5,472,442 A 12/1995 Klicek
5,472,443 A 12/1995 Cordis et al.
5,478,351 A 12/1995 Meade et al.
5,480,406 A 1/1996 Nolan et al.
5,480,409 A 1/1996 Riza
5,484,436 A 1/1996 Eggers et al.
5,496,312 A 3/1996 Klicek
5,496,317 A 3/1996 Goble et al.
5,496,347 A 3/1996 Hashiguchi et al.
5,499,997 A 3/1996 Sharpe et al.
5,509,922 A 4/1996 Aranyi et al.
5,512,721 A 4/1996 Young et al.
5,514,134 A 5/1996 Rydell et al.
5,527,313 A 6/1996 Scott et al.
5,528,833 A 6/1996 Sakuma
5,529,067 A 6/1996 Larsen et al.
5,531,744 A 7/1996 Nardella et al.
5,536,251 A 7/1996 Evard et al.
5,540,684 A 7/1996 Hassler, Jr.
5,540,685 A 7/1996 Parins et al.
5,540,706 A 7/1996 Aust et al.
5,540,715 A 7/1996 Katsaros et al.
5,542,945 A 8/1996 Fritzsch
5,558,671 A 9/1996 Yates
5,558,672 A 9/1996 Edwards et al.
5,562,619 A 10/1996 Mirarchi et al.
5,562,699 A 10/1996 Heimberger et al.
5,562,720 A 10/1996 Stern et al.
5,564,615 A 10/1996 Bishop et al.
5,569,241 A 10/1996 Edwards
5,569,243 A 10/1996 Kortenbach et al.
5,571,100 A 11/1996 Goble et al.
5,573,424 A 11/1996 Poppe
5,573,534 A 11/1996 Stone
5,573,535 A 11/1996 Viklund
5,575,799 A 11/1996 Bolanos et al.
5,575,805 A 11/1996 Li
5,578,052 A 11/1996 Koros et al.
5,579,781 A 12/1996 Cooke
5,582,611 A 12/1996 Tsuruta et al.
5,582,617 A 12/1996 Klieman et al.
5,585,896 A 12/1996 Yamazaki et al.
5,590,570 A 1/1997 LeMaire, III et al.
5,591,181 A 1/1997 Stone et al.
5,597,107 A 1/1997 Knodel et al.
5,601,224 A 2/1997 Bishop et al.
5,601,601 A 2/1997 Tal et al.
5,601,641 A 2/1997 Stephens
5,603,711 A 2/1997 Parins et al.
5,603,723 A 2/1997 Aranyi et al.
5,611,798 A 3/1997 Eggers
5,611,808 A 3/1997 Hossain et al.
5,611,813 A 3/1997 Lichtman
5,620,415 A 4/1997 Lucey et al.
5,620,453 A 4/1997 Nallakrishnan
5,620,459 A 4/1997 Lichtman
5,624,452 A 4/1997 Yates
5,626,578 A 5/1997 Tihon
5,626,609 A 5/1997 Zvenyatsky et al.
5,630,833 A 5/1997 Katsaros et al.
5,637,110 A 6/1997 Pennybacker et al.
5,638,003 A 6/1997 Hall
5,643,294 A 7/1997 Tovey et al.
5,647,869 A 7/1997 Goble et al.
5,647,871 A 7/1997 Levine et al.
5,649,959 A 7/1997 Hannam et al.
5,655,650 A 8/1997 Naitou
5,658,281 A 8/1997 Heard
D384,413 S 9/1997 Zlock et al.
5,662,667 A 9/1997 Knodel
5,665,100 A 9/1997 Yoon
5,667,526 A 9/1997 Levin
5,674,220 A 10/1997 Fox et al.
5,674,229 A 10/1997 Tovey et al.
5,681,282 A 10/1997 Eggers et al.
5,688,270 A 11/1997 Yates et al.
5,690,652 A 11/1997 Wurster et al.
5,690,653 A 11/1997 Richardson et al.
5,693,051 A 12/1997 Schulze et al. .. A61B 17/07207 606/41
5,693,920 A 12/1997 Maeda
5,695,522 A 12/1997 LeMaire, III et al.

(56) References Cited

U.S. PATENT DOCUMENTS 5,700,261 A 12/1997 Brinkerhoff
5,700,270 A 12/1997 Peyser et al.
5,702,390 A 12/1997 Austin et al.
5,707,369 A 1/1998 Vaitekunas et al.
5,709,680 A 1/1998 Yates et al.
5,716,366 A 2/1998 Yates
5,720,744 A 2/1998 Eggleston et al.
5,722,421 A 3/1998 Francese et al.
5,725,536 A 3/1998 Oberlin et al.
5,727,428 A 3/1998 LeMaire, III et al.
5,735,848 A 4/1998 Yates et al.
5,743,906 A 4/1998 Parins et al.
5,752,973 A 5/1998 Kieturakis
5,755,717 A 5/1998 Yates et al.
5,759,188 A 6/1998 Yoon
5,766,130 A 6/1998 Selmonosky
5,766,166 A 6/1998 Hooven
5,766,170 A 6/1998 Eggers
5,766,196 A 6/1998 Griffiths
5,769,849 A 6/1998 Eggers
5,772,655 A 6/1998 Bauer et al.
5,772,670 A 6/1998 Brosa
5,776,128 A 7/1998 Eggers
5,776,130 A 7/1998 Buysse et al.
5,779,646 A 7/1998 Koblish et al.
5,779,701 A 7/1998 McBrayer et al.
H1745 H 8/1998 Paraschac
5,792,137 A 8/1998 Carr et al.
5,792,165 A 8/1998 Klieman et al.
5,792,177 A 8/1998 Kaseda
5,797,537 A 8/1998 Oberlin et al.
5,797,927 A 8/1998 Yoon
5,797,938 A 8/1998 Paraschac et al.
5,797,941 A 8/1998 Schulze et al.
5,797,958 A 8/1998 Yoon
5,800,449 A 9/1998 Wales
5,807,393 A 9/1998 Williamson, IV et al.
5,810,764 A 9/1998 Eggers et al.
5,810,805 A 9/1998 Sutcu et al.
5,810,808 A 9/1998 Eggers
5,810,811 A 9/1998 Yates et al.
5,810,877 A 9/1998 Roth et al.
5,814,043 A 9/1998 Shapeton
5,814,054 A 9/1998 Kortenbach et al.
5,817,083 A 10/1998 Shemesh et al.
5,817,093 A 10/1998 Williamson, IV et al.
5,817,119 A 10/1998 Klieman et al.
5,820,630 A 10/1998 Lind
5,824,978 A 10/1998 Karasik et al.
5,827,271 A 10/1998 Buysse et al.
5,827,279 A 10/1998 Hughett et al.
5,827,281 A 10/1998 Levin
5,827,323 A 10/1998 Klieman et al.
5,827,548 A 10/1998 Lavallee et al.
5,833,690 A 11/1998 Yates et al.
5,843,080 A 12/1998 Fleenor et al.
5,849,022 A 12/1998 Sakashita et al.
5,853,412 A 12/1998 Mayenberger
5,859,527 A 1/1999 Cook
5,860,976 A 1/1999 Billings et al.
5,876,401 A 3/1999 Schulze et al.
5,876,412 A 3/1999 Piraka
5,882,567 A 3/1999 Cavallaro et al.
5,891,141 A 4/1999 Rydell
5,891,142 A 4/1999 Eggers et al.
5,893,863 A 4/1999 Yoon
5,893,875 A 4/1999 O'Connor et al.
5,893,877 A 4/1999 Gampp, Jr. et al.
5,897,563 A 4/1999 Yoon et al.
5,902,301 A 5/1999 Olig
5,906,630 A 5/1999 Anderhub et al.
5,908,420 A 6/1999 Parins et al.
5,908,432 A 6/1999 Pan
5,911,719 A 6/1999 Eggers
5,913,874 A 6/1999 Berns et al.
5,921,916 A 7/1999 Aeikens et al.
5,921,984 A 7/1999 Sutcu et al.
5,925,043 A 7/1999 Kumar et al.
5,928,136 A 7/1999 Barry
5,935,126 A 8/1999 Riza
5,941,869 A 8/1999 Patterson et al.
5,944,718 A 8/1999 Austin et al.
5,951,546 A 9/1999 Lorentzen
5,951,549 A 9/1999 Richardson et al.
5,954,720 A 9/1999 Wilson et al.
5,954,731 A 9/1999 Yoon
5,954,733 A 9/1999 Yoon
5,957,923 A 9/1999 Hahnen et al.
5,957,937 A 9/1999 Yoon
5,960,544 A 10/1999 Beyers
5,961,514 A 10/1999 Long et al.
5,964,758 A 10/1999 Dresden
5,976,132 A 11/1999 Morris
5,984,932 A 11/1999 Yoon
5,984,938 A 11/1999 Yoon
5,984,939 A 11/1999 Yoon
5,989,277 A 11/1999 LeMaire, III et al.
5,993,466 A 11/1999 Yoon
5,993,467 A 11/1999 Yoon
5,997,565 A 12/1999 Inoue
6,004,332 A 12/1999 Yoon et al.
6,004,335 A 12/1999 Vaitekunas et al.
6,010,516 A 1/2000 Hulka et al.
6,017,358 A 1/2000 Yoon et al.
6,021,693 A 2/2000 Feng-Sing
6,024,741 A 2/2000 Williamson et al.
6,024,743 A 2/2000 Edwards
6,024,744 A 2/2000 Kese et al.
6,027,522 A 2/2000 Palmer
6,030,384 A 2/2000 Nezhat
6,033,399 A 3/2000 Gines
6,039,733 A 3/2000 Buysse et al.
6,041,679 A 3/2000 Slater et al.
6,050,996 A * 4/2000 Schmaltz et al. ..... 606/51
6,053,914 A 4/2000 Eggers et al.
6,053,933 A 4/2000 Balazs et al.
D424,694 S 5/2000 Tetzlaff et al.
D425,201 S 5/2000 Tetzlaff et al.
6,059,782 A 5/2000 Novak et al.
6,066,139 A 5/2000 Ryan et al.
6,074,386 A 6/2000 Goble et al.
6,077,287 A 6/2000 Taylor et al.
6,080,180 A 6/2000 Yoon et al.
RE36,795 E 7/2000 Rydell
6,083,223 A 7/2000 Baker
6,086,586 A 7/2000 Hooven
6,086,601 A 7/2000 Yoon
6,090,107 A 7/2000 Borgmeier et al.
6,096,031 A 8/2000 Mitchell et al.
6,096,037 A 8/2000 Mulier et al.
6,099,550 A 8/2000 Yoon
6,102,909 A 8/2000 Chen et al.
6,106,542 A 8/2000 Toybin et al.
6,110,171 A 8/2000 Rydell
6,113,596 A 9/2000 Hooven et al.
6,113,598 A 9/2000 Baker
6,117,158 A 9/2000 Measamer et al.
6,122,549 A 9/2000 Sharkey et al.
6,123,701 A 9/2000 Nezhat
H1904 H 10/2000 Yates et al.
6,126,658 A 10/2000 Baker
6,126,665 A 10/2000 Yoon
6,139,563 A 10/2000 Cosgrove, III et al.
6,143,005 A 11/2000 Yoon et al.
6,152,923 A 11/2000 Ryan
6,162,220 A 12/2000 Nezhat
6,171,316 B1 1/2001 Kovac et al.
6,174,309 B1 1/2001 Wrublewski et al.
6,178,628 B1 1/2001 Clemens et al.
6,179,834 B1 1/2001 Buysse et al.
6,179,837 B1 1/2001 Hooven
6,183,467 B1 2/2001 Shapeton et al.
6,187,003 B1 2/2001 Buysse et al.
6,190,386 B1 2/2001 Rydell

(56) References Cited

U.S. PATENT DOCUMENTS

| | | | |
|---|---|---|---|
| 6,190,400 | B1 | 2/2001 | VanDeMoer et al. |
| 6,193,718 | B1 | 2/2001 | Kortenbach et al. |
| 6,206,876 | B1 | 3/2001 | Levine et al. |
| 6,206,877 | B1 | 3/2001 | Kese et al. |
| 6,206,893 | B1 | 3/2001 | Klein et al. |
| 6,214,028 | B1 | 4/2001 | Yoon et al. |
| 6,217,602 | B1 | 4/2001 | Redmon |
| 6,217,615 | B1 | 4/2001 | Sioshansi et al. |
| 6,221,039 | B1 | 4/2001 | Durgin et al. |
| 6,223,100 | B1 | 4/2001 | Green |
| 6,224,593 | B1 | 5/2001 | Ryan et al. |
| 6,224,614 | B1 | 5/2001 | Yoon |
| 6,228,080 | B1 | 5/2001 | Gines |
| 6,228,083 | B1 | 5/2001 | Lands et al. |
| 6,248,124 | B1 | 6/2001 | Pedros et al. |
| 6,248,944 | B1 | 6/2001 | Ito |
| 6,261,307 | B1 | 7/2001 | Yoon et al. |
| 6,267,761 | B1 | 7/2001 | Ryan |
| 6,270,497 | B1 | 8/2001 | Sekino et al. |
| 6,270,508 | B1 | 8/2001 | Klieman et al. |
| 6,273,887 | B1 | 8/2001 | Yamauchi et al. |
| 6,277,117 | B1 | 8/2001 | Tetzlaff et al. |
| 6,280,458 | B1 | 8/2001 | Boche et al. |
| 6,283,961 | B1 | 9/2001 | Underwood et al. |
| D449,886 | S | 10/2001 | Tetzlaff et al. |
| 6,298,550 | B1 | 10/2001 | Kirwan |
| 6,302,424 | B1 | 10/2001 | Gisinger et al. |
| 6,319,262 | B1 | 11/2001 | Bates et al. |
| 6,319,451 | B1 | 11/2001 | Brune |
| 6,322,561 | B1 | 11/2001 | Eggers et al. |
| 6,322,580 | B1 | 11/2001 | Kanner |
| 6,325,795 | B1 | 12/2001 | Lindemann et al. |
| 6,334,860 | B1 | 1/2002 | Dorn |
| 6,334,861 | B1 | 1/2002 | Chandler et al. |
| 6,345,532 | B1 | 2/2002 | Coudray et al. |
| 6,350,264 | B1 | 2/2002 | Hooven |
| 6,352,536 | B1 | 3/2002 | Buysse et al. |
| 6,358,249 | B1 | 3/2002 | Chen et al. |
| 6,358,259 | B1 | 3/2002 | Swain et al. |
| 6,358,268 | B1 | 3/2002 | Hunt et al. |
| 6,364,879 | B1 | 4/2002 | Chen et al. |
| D457,958 | S | 5/2002 | Dycus et al. |
| D457,959 | S | 5/2002 | Tetzlaff et al. |
| 6,387,094 | B1 | 5/2002 | Eitenmuller |
| 6,391,035 | B1 | 5/2002 | Appleby et al. |
| 702,472 | A1 | 6/2002 | Pignolet |
| 6,398,779 | B1 | 6/2002 | Buysse et al. |
| 6,402,747 | B1 | 6/2002 | Lindemann et al. |
| 6,409,728 | B1 | 6/2002 | Ehr et al. |
| H2037 | H | 7/2002 | Yates et al. |
| 6,419,675 | B1 | 7/2002 | Gallo, Sr. |
| 6,425,896 | B1 | 7/2002 | Baltschun et al. |
| 6,432,112 | B2 | 8/2002 | Brock et al. |
| 6,440,144 | B1 | 8/2002 | Bacher |
| 6,443,952 | B1 | 9/2002 | Mulier et al. |
| 6,443,970 | B1 | 9/2002 | Schulze et al. |
| 6,451,018 | B1 | 9/2002 | Lands et al. |
| 6,458,125 | B1 | 10/2002 | Cosmescu |
| 6,458,128 | B1 | 10/2002 | Schulze |
| 6,458,130 | B1 | 10/2002 | Frazier et al. |
| 6,461,352 | B2 | 10/2002 | Morgan et al. |
| 6,461,368 | B2 | 10/2002 | Fogarty et al. |
| 6,464,701 | B1 | 10/2002 | Hooven et al. |
| 6,464,702 | B2 | 10/2002 | Schulze et al. |
| 6,464,704 | B2 | 10/2002 | Schmaltz et al. |
| 6,485,489 | B2 | 11/2002 | Teirstein et al. |
| 6,494,888 | B1 | 12/2002 | Laufer et al. |
| 6,500,176 | B1 | 12/2002 | Truckai et al. |
| 6,503,248 | B1 | 1/2003 | Levine |
| 6,506,189 | B1 | 1/2003 | Rittman et al. |
| 6,506,196 | B1 | 1/2003 | Laufer |
| 6,508,815 | B1 | 1/2003 | Strul et al. |
| 6,511,480 | B1 | 1/2003 | Tetzlaff et al. |
| 6,514,215 | B1 | 2/2003 | Ouchi |
| 6,514,251 | B1 | 2/2003 | Ni et al. |
| 6,514,252 | B2 | 2/2003 | Nezhat et al. |
| 6,517,539 | B1 | 2/2003 | Smith et al. |
| 6,527,771 | B1 | 3/2003 | Weadock et al. |
| 6,533,784 | B2 | 3/2003 | Truckai et al. |
| 6,544,264 | B2 | 4/2003 | Levine et al. |
| 6,545,239 | B2 | 4/2003 | Pedersen et al. |
| 728,883 | A1 | 5/2003 | Downes |
| 6,558,385 | B1 | 5/2003 | McClurken et al. |
| 6,562,037 | B2 * | 5/2003 | Paton et al. ..... 606/51 |
| 6,569,105 | B1 | 5/2003 | Kortenbach et al. |
| 6,569,162 | B2 | 5/2003 | He |
| 6,582,450 | B2 | 6/2003 | Ouchi |
| 6,585,735 | B1 | 7/2003 | Frazier et al. |
| 6,602,252 | B2 | 8/2003 | Mollenauer |
| 6,605,790 | B2 | 8/2003 | Yoshida |
| 6,616,658 | B2 | 9/2003 | Ineson |
| 6,616,661 | B2 | 9/2003 | Wellman et al. |
| 6,620,161 | B2 | 9/2003 | Schulze et al. |
| 6,620,184 | B2 | 9/2003 | De Laforcade et al. |
| 6,626,901 | B1 | 9/2003 | Treat et al. |
| 6,638,287 | B2 | 10/2003 | Danitz et al. |
| 6,641,595 | B1 | 11/2003 | Moran et al. |
| 6,652,514 | B2 | 11/2003 | Ellman et al. |
| 6,652,521 | B2 | 11/2003 | Schulze |
| 6,656,175 | B2 | 12/2003 | Francischelli et al. |
| 6,656,177 | B2 | 12/2003 | Truckai et al. |
| 6,660,072 | B2 | 12/2003 | Chatterjee |
| 6,663,639 | B1 | 12/2003 | Laufer et al. |
| 6,663,641 | B1 | 12/2003 | Kovac et al. |
| 6,666,854 | B1 | 12/2003 | Lange |
| 6,669,696 | B2 | 12/2003 | Bacher et al. |
| 6,673,092 | B1 | 1/2004 | Bacher |
| 6,676,660 | B2 | 1/2004 | Wampler et al. |
| 6,676,676 | B2 | 1/2004 | Danitz et al. |
| 6,679,882 | B1 | 1/2004 | Kornerup |
| 6,682,527 | B2 | 1/2004 | Strul |
| 6,682,528 | B2 | 1/2004 | Frazier et al. |
| 6,685,724 | B1 | 2/2004 | Haluck |
| 6,689,131 | B2 | 2/2004 | McClurken |
| 6,692,445 | B2 | 2/2004 | Roberts et al. |
| 6,693,246 | B1 | 2/2004 | Rudolph et al. |
| 6,695,840 | B2 | 2/2004 | Schulze |
| 6,702,810 | B2 | 3/2004 | McClurken et al. |
| 6,723,092 | B2 | 4/2004 | Brown et al. |
| 6,726,068 | B2 | 4/2004 | Miller |
| 6,726,686 | B2 | 4/2004 | Buysse et al. |
| 6,726,694 | B2 | 4/2004 | Blatter et al. |
| 6,733,498 | B2 | 5/2004 | Paton et al. |
| 6,736,813 | B2 | 5/2004 | Yamauchi et al. |
| 6,743,229 | B2 | 6/2004 | Buysse et al. |
| 6,743,230 | B2 | 6/2004 | Lutze et al. |
| 6,743,239 | B1 | 6/2004 | Kuehn et al. |
| 6,743,240 | B2 | 6/2004 | Smith et al. |
| 6,755,843 | B2 | 6/2004 | Chung et al. |
| 6,756,553 | B1 | 6/2004 | Yamaguchi et al. |
| 6,757,977 | B2 | 7/2004 | Dambal et al. |
| D493,888 | S | 8/2004 | Reschke |
| 6,770,072 | B1 | 8/2004 | Truckai et al. |
| 6,773,409 | B2 | 8/2004 | Truckai et al. |
| 6,773,432 | B1 | 8/2004 | Clayman et al. |
| 6,773,434 | B2 | 8/2004 | Ciarrocca |
| 6,773,441 | B1 | 8/2004 | Laufer et al. |
| 6,775,575 | B2 | 8/2004 | Bommannan et al. |
| 6,776,780 | B2 | 8/2004 | Mulier et al. |
| 6,786,905 | B2 | 9/2004 | Swanson et al. |
| 6,790,217 | B2 | 9/2004 | Schulze et al. |
| 6,796,981 | B2 | 9/2004 | Wham et al. |
| D496,997 | S | 10/2004 | Dycus et al. |
| 6,800,825 | B1 | 10/2004 | Sasaki et al. |
| 6,802,843 | B2 | 10/2004 | Truckai et al. |
| 6,808,525 | B2 | 10/2004 | Latterell et al. |
| D499,181 | S | 11/2004 | Dycus et al. |
| 6,818,000 | B2 | 11/2004 | Muller et al. |
| 6,821,285 | B2 | 11/2004 | Laufer et al. |
| 6,835,200 | B2 | 12/2004 | Laufer et al. |
| 6,857,357 | B2 | 2/2005 | Fujii |
| 6,860,880 | B2 | 3/2005 | Treat et al. |
| 6,887,240 | B1 | 5/2005 | Lands et al. |
| 6,889,116 | B2 | 5/2005 | Jinno |

(56) References Cited

U.S. PATENT DOCUMENTS

| | | | |
|---|---|---|---|
| 6,914,201 | B2 | 7/2005 | Van Vooren et al. |
| 6,926,716 | B2 | 8/2005 | Baker et al. |
| 6,929,644 | B2 | 8/2005 | Truckai et al. |
| 6,932,810 | B2 | 8/2005 | Ryan |
| 6,932,816 | B2 | 8/2005 | Phan |
| 6,934,134 | B2 | 8/2005 | Mori et al. |
| 6,936,061 | B2 | 8/2005 | Sasaki |
| D509,297 | S | 9/2005 | Wells |
| 6,942,662 | B2 | 9/2005 | Goble et al. |
| 6,943,311 | B2 | 9/2005 | Miyako |
| 6,953,430 | B2 | 10/2005 | Kodooka |
| 6,953,461 | B2 | 10/2005 | McClurken et al. |
| 6,958,070 | B2 | 10/2005 | Witt et al. |
| 6,960,210 | B2 | 11/2005 | Lands et al. |
| 6,964,662 | B2 | 11/2005 | Kidooka |
| 6,966,907 | B2 | 11/2005 | Goble |
| 6,972,017 | B2 | 12/2005 | Smith et al. |
| 6,977,495 | B2 | 12/2005 | Donofrio |
| 6,979,786 | B2 | 12/2005 | Aukland et al. |
| 6,981,628 | B2 | 1/2006 | Wales |
| 6,987,244 | B2 | 1/2006 | Bauer |
| 6,994,707 | B2 | 2/2006 | Ellman et al. |
| 6,994,709 | B2 | 2/2006 | Iida |
| 6,997,931 | B2 | 2/2006 | Sauer et al. |
| 7,001,381 | B2 | 2/2006 | Harano et al. |
| 7,011,657 | B2 | 3/2006 | Truckai et al. |
| 7,033,354 | B2 | 4/2006 | Keppel |
| 7,033,356 | B2 | 4/2006 | Latterell et al. |
| 7,041,102 | B2 | 5/2006 | Truckai et al. |
| 7,044,948 | B2 | 5/2006 | Keppel |
| 7,052,489 | B2 | 5/2006 | Griego et al. |
| 7,052,496 | B2 | 5/2006 | Yamauchi |
| 7,063,715 | B2 | 6/2006 | Onuki et al. |
| D525,361 | S | 7/2006 | Hushka |
| 7,070,597 | B2 | 7/2006 | Truckai et al. |
| 7,083,618 | B2 | 8/2006 | Couture et al. |
| 7,083,619 | B2 | 8/2006 | Truckai et al. |
| 7,083,620 | B2 | 8/2006 | Jahns et al. |
| 7,087,051 | B2 | 8/2006 | Bourne et al. |
| 7,087,054 | B2 | 8/2006 | Truckai et al. |
| 7,090,673 | B2 | 8/2006 | Dycus et al. |
| 7,090,689 | B2 | 8/2006 | Nagase et al. |
| 7,101,371 | B2 | 9/2006 | Dycus et al. |
| 7,101,372 | B2 | 9/2006 | Dycus et al. |
| 7,101,373 | B2 | 9/2006 | Dycus et al. |
| 7,103,947 | B2 | 9/2006 | Sartor et al. |
| 7,107,124 | B2 | 9/2006 | Green |
| 7,112,199 | B2 | 9/2006 | Cosmescu |
| D531,311 | S | 10/2006 | Guerra et al. |
| 7,115,123 | B2 | 10/2006 | Knowlton et al. |
| 7,118,570 | B2 | 10/2006 | Tetzlaff et al. |
| 7,118,587 | B2 | 10/2006 | Dycus et al. |
| 7,131,860 | B2 | 11/2006 | Sartor et al. |
| 7,131,970 | B2 | 11/2006 | Moses et al. |
| 7,131,971 | B2 | 11/2006 | Dycus et al. |
| 7,135,020 | B2 | 11/2006 | Lawes et al. |
| D533,942 | S | 12/2006 | Kerr et al. |
| 7,145,757 | B2 | 12/2006 | Shea et al. |
| 7,147,638 | B2 | 12/2006 | Chapman et al. |
| 7,150,097 | B2 | 12/2006 | Sremcich et al. |
| 7,150,749 | B2 | 12/2006 | Dycus et al. |
| 7,153,314 | B2 | 12/2006 | Laufer et al. |
| D535,027 | S | 1/2007 | James et al. |
| 7,156,842 | B2 | 1/2007 | Sartor et al. |
| 7,156,846 | B2 | 1/2007 | Dycus et al. |
| 7,160,298 | B2 | 1/2007 | Lawes et al. |
| 7,160,299 | B2 | 1/2007 | Baily |
| 7,169,146 | B2 | 1/2007 | Truckai et al. |
| 7,179,255 | B2 | 2/2007 | Lettice et al. |
| 7,179,258 | B2 | 2/2007 | Buysse et al. |
| 7,195,631 | B2 | 3/2007 | Dumbauld |
| D541,418 | S | 4/2007 | Schechter et al. |
| 7,207,990 | B2 | 4/2007 | Lands et al. |
| D541,938 | S | 5/2007 | Kerr et al |
| 7,223,264 | B2 | 5/2007 | Daniel et al. |
| 7,223,265 | B2 | 5/2007 | Keppel |
| 7,232,440 | B2 | 6/2007 | Dumbauld et al. |
| 7,241,288 | B2 | 7/2007 | Braun |
| 7,241,296 | B2 | 7/2007 | Buysse et al. |
| 7,244,257 | B2 | 7/2007 | Podjahsky et al. |
| 7,246,734 | B2 | 7/2007 | Shelto, IV |
| 7,248,944 | B2 | 7/2007 | Green |
| 7,252,667 | B2 | 8/2007 | Moses et al. |
| 7,255,697 | B2 | 8/2007 | Dycus et al. |
| 7,267,677 | B2 | 9/2007 | Johnson et al. |
| 7,270,660 | B2 | 9/2007 | Ryan |
| 7,270,664 | B2 | 9/2007 | Johnson et al. |
| 7,276,068 | B2 | 10/2007 | Johnson et al. |
| 7,300,435 | B2 | 11/2007 | Wham et al. |
| 7,303,557 | B2 | 12/2007 | Wham et al. |
| 7,311,709 | B2 | 12/2007 | Truckai et al. |
| 7,314,471 | B2 | 1/2008 | Holman |
| 7,318,823 | B2 | 1/2008 | Sharps et al. |
| 7,329,256 | B2 | 2/2008 | Johnson et al. |
| 7,329,257 | B2 | 2/2008 | Kanehira et al. |
| D564,662 | S | 3/2008 | Moses et al. |
| 7,338,526 | B2 | 3/2008 | Steinberg |
| 7,342,754 | B2 | 3/2008 | Fitzgerald et al. |
| 7,344,268 | B2 | 3/2008 | Jhigamian |
| D567,943 | S | 4/2008 | Moses et al. |
| 7,367,976 | B2 | 5/2008 | Lawes et al. |
| 7,377,920 | B2 | 5/2008 | Buysse et al. |
| 7,384,420 | B2 | 6/2008 | Dycus et al. |
| 7,384,421 | B2 | 6/2008 | Hushka |
| 7,396,336 | B2 | 7/2008 | Orszulak et al. |
| D575,395 | S | 8/2008 | Hushka |
| D575,401 | S | 8/2008 | Hixson et al. |
| 7,435,249 | B2 | 10/2008 | Buysse et al. |
| 7,442,193 | B2 | 10/2008 | Shields et al. |
| 7,442,194 | B2 | 10/2008 | Dumbauld et al. |
| 7,445,621 | B2 | 11/2008 | Dumbauld et al. |
| 7,458,972 | B2 | 12/2008 | Keppel |
| 7,473,253 | B2 | 1/2009 | Dycus et al. |
| 7,481,810 | B2 | 1/2009 | Dumbauld et al. |
| 7,487,780 | B2 | 2/2009 | Hooven |
| 7,491,201 | B2 | 2/2009 | Shields et al. |
| 7,491,202 | B2 | 2/2009 | Odom et al. |
| 7,500,975 | B2 | 3/2009 | Cunningham et al. |
| 7,510,556 | B2 | 3/2009 | Nguyen et al. |
| 7,513,898 | B2 | 4/2009 | Johnson et al. |
| 7,540,872 | B2 | 6/2009 | Schechter et al. |
| 7,549,995 | B2 | 6/2009 | Schultz |
| 7,553,312 | B2 | 6/2009 | Tetzlaff et al. |
| 8,016,827 | B2 | 9/2011 | Chojin |
| 8,114,122 | B2 | 2/2012 | Nau, Jr. |
| 8,142,473 | B2 | 3/2012 | Cunningham |
| 8,162,973 | B2 | 4/2012 | Cunningham |
| 8,197,479 | B2 | 6/2012 | Olson et al. |
| 8,226,650 | B2 | 7/2012 | Kerr |
| 8,251,994 | B2 | 8/2012 | McKenna et al. |
| 8,257,387 | B2 | 9/2012 | Cunningham |
| 8,282,634 | B2 | 10/2012 | Cunningham et al. |
| 2002/0013583 | A1 | 1/2002 | Camran et al. |
| 2002/0049442 | A1 | 4/2002 | Roberts et al. |
| 2002/0099372 | A1 | 7/2002 | Schulze et al. |
| 2002/0107517 | A1 | 8/2002 | Witt et al. |
| 2002/0111624 | A1 | 8/2002 | Witt et al. |
| 2002/0188294 | A1 | 12/2002 | Couture et al. |
| 2003/0014052 | A1 | 1/2003 | Buysse et al. |
| 2003/0014053 | A1 | 1/2003 | Nguyen et al. |
| 2003/0018331 | A1 | 1/2003 | Dycus et al. |
| 2003/0018332 | A1 | 1/2003 | Schmaltz et al. |
| 2003/0069570 | A1 | 4/2003 | Witzel et al. |
| 2003/0069571 | A1 | 4/2003 | Treat et al. |
| 2003/0078578 | A1 | 4/2003 | Truckai et al. |
| 2003/0109875 | A1 | 6/2003 | Tetzlaff et al. |
| 2003/0114851 | A1 | 6/2003 | Truckai et al. |
| 2003/0139741 | A1 | 7/2003 | Goble et al. |
| 2003/0139742 | A1 | 7/2003 | Wampler et al. |
| 2003/0158548 | A1 | 8/2003 | Phan et al. |
| 2003/0158549 | A1 | 8/2003 | Swanson |
| 2003/0171747 | A1 | 9/2003 | Kanehira et al. |
| 2003/0181910 | A1 | 9/2003 | Dycus et al. |
| 2003/0199869 | A1 | 10/2003 | Johnson et al. |

(56) References Cited

U.S. PATENT DOCUMENTS

2003/0216732 A1 11/2003 Truckai et al.
2003/0220637 A1 11/2003 Truckai et al.
2003/0229344 A1 12/2003 Dycus et al.
2003/0236325 A1 12/2003 Bonora
2003/0236518 A1 12/2003 Marchitto et al.
2004/0030330 A1 2/2004 Brassell et al.
2004/0030332 A1 2/2004 Knowlton et al.
2004/0049185 A1 3/2004 Latterell et al.
2004/0064151 A1 4/2004 Mollenauer
2004/0073238 A1 4/2004 Makower
2004/0073256 A1 4/2004 Marchitto et al.
2004/0078035 A1 4/2004 Kanehira et al.
2004/0115296 A1 6/2004 Duffin
2004/0116979 A1 6/2004 Truckai et al.
2004/0122423 A1* 6/2004 Dycus ..... A61B 18/1445 606/51
2004/0143263 A1 7/2004 Schechter et al.
2004/0147925 A1 7/2004 Buysse et al.
2004/0148035 A1 7/2004 Barrett et al.
2004/0162557 A1 8/2004 Tetzlaff et al.
2004/0199181 A1 10/2004 Knodel et al.
2004/0210282 A1 10/2004 Flock et al.
2004/0224590 A1 11/2004 Rawa et al.
2004/0225288 A1 11/2004 Buysse et al.
2004/0230189 A1 11/2004 Keppel
2004/0236325 A1 11/2004 Tetzlaff et al.
2004/0236326 A1 11/2004 Schulze et al.
2004/0243125 A1 12/2004 Dycus et al.
2004/0249371 A1 12/2004 Dycus et al.
2004/0249374 A1 12/2004 Tetzlaff et al.
2004/0250419 A1 12/2004 Sremcich et al.
2004/0254573 A1 12/2004 Dycus et al.
2004/0260281 A1 12/2004 Baxter, III et al.
2005/0004564 A1 1/2005 Wham et al.
2005/0004568 A1 1/2005 Lawes et al.
2005/0004569 A1 1/2005 Witt et al.
2005/0004570 A1 1/2005 Chapman et al.
2005/0021025 A1 1/2005 Buysse et al.
2005/0021026 A1 1/2005 Baily
2005/0021027 A1 1/2005 Shields et al.
2005/0033278 A1 2/2005 McClurken et al.
2005/0059934 A1 3/2005 Wenchell et al.
2005/0096645 A1 5/2005 Wellman et al.
2005/0101951 A1 5/2005 Wham et al.
2005/0101952 A1 5/2005 Lands et al.
2005/0107784 A1 5/2005 Moses et al.
2005/0107785 A1 5/2005 Dycus et al.
2005/0113818 A1 5/2005 Sartor et al.
2005/0113819 A1 5/2005 Wham et al.
2005/0113826 A1 5/2005 Johnson et al.
2005/0113827 A1 5/2005 Dumbauld et al.
2005/0113828 A1 5/2005 Shields et al.
2005/0119655 A1 6/2005 Moses et al.
2005/0137590 A1 6/2005 Lawes et al.
2005/0149017 A1 7/2005 Dycus
2005/0149151 A1 7/2005 Orszulak et al.
2005/0154387 A1 7/2005 Moses et al.
2005/0187547 A1 8/2005 Sugi
2005/0197659 A1 9/2005 Bahney
2005/0203504 A1 9/2005 Wham et al.
2005/0240179 A1 10/2005 Buysse et al.
2006/0052778 A1 3/2006 Chapman et al.
2006/0052779 A1 3/2006 Hammill
2006/0064085 A1 3/2006 Schechter et al.
2006/0064086 A1 3/2006 Odom
2006/0074417 A1 4/2006 Cunningham et al.
2006/0079888 A1 4/2006 Mulier et al.
2006/0079890 A1 4/2006 Guerra
2006/0079891 A1 4/2006 Arts et al.
2006/0079933 A1 4/2006 Hushka et al.
2006/0084973 A1 4/2006 Hushka
2006/0089670 A1 4/2006 Hushka
2006/0116675 A1 6/2006 McClurken et al.
2006/0129146 A1 6/2006 Dycus et al.
2006/0161150 A1 7/2006 Keppel
2006/0167450 A1 7/2006 Johnson et al.
2006/0167452 A1 7/2006 Moses et al.
2006/0173452 A1 8/2006 Buysse et al.
2006/0189980 A1 8/2006 Johnson et al.
2006/0189981 A1 8/2006 Dycus et al.
2006/0190035 A1 8/2006 Hushka et al.
2006/0217709 A1 9/2006 Couture et al.
2006/0224158 A1 10/2006 Odom et al.
2006/0229666 A1 10/2006 Suzuki et al.
2006/0253126 A1 11/2006 Bjerken et al.
2006/0259036 A1 11/2006 Tetzlaff et al.
2006/0264922 A1 11/2006 Sartor et al.
2006/0264931 A1 11/2006 Chapman et al.
2006/0271038 A1 11/2006 Johnson et al.
2006/0283093 A1 12/2006 Petrovic et al.
2006/0287641 A1 12/2006 Perlin
2007/0016182 A1 1/2007 Lipson et al.
2007/0016187 A1 1/2007 Weinberg et al.
2007/0043352 A1 2/2007 Garrison et al.
2007/0043353 A1 2/2007 Dycus et al.
2007/0055231 A1 3/2007 Dycus et al.
2007/0060919 A1 3/2007 Isaacson et al.
2007/0062017 A1 3/2007 Dycus et al.
2007/0074807 A1 4/2007 Guerra
2007/0078456 A1 4/2007 Dumbauld et al.
2007/0078458 A1 4/2007 Dumbauld et al.
2007/0078459 A1 4/2007 Johnson et al.
2007/0088356 A1 4/2007 Moses et al.
2007/0106295 A1 5/2007 Garrison et al.
2007/0106297 A1 5/2007 Dumbauld et al.
2007/0118111 A1 5/2007 Weinberg
2007/0118115 A1 5/2007 Artale et al.
2007/0142833 A1 6/2007 Dycus et al.
2007/0142834 A1 6/2007 Dumbauld
2007/0156139 A1 7/2007 Schechter et al.
2007/0156140 A1 7/2007 Baily
2007/0173811 A1 7/2007 Couture et al.
2007/0173814 A1 7/2007 Hixson et al.
2007/0179499 A1 8/2007 Garrison
2007/0198011 A1 8/2007 Sugita
2007/0203485 A1 8/2007 Keppel
2007/0213706 A1 9/2007 Dumbauld et al.
2007/0213707 A1 9/2007 Dumbauld et al.
2007/0213708 A1 9/2007 Dumbauld et al.
2007/0213712 A1 9/2007 Buysse et al.
2007/0255279 A1 11/2007 Buysse et al.
2007/0260235 A1 11/2007 Podhajsky
2007/0260238 A1 11/2007 Guerra
2007/0260241 A1 11/2007 Dalla Betta et al.
2007/0260242 A1 11/2007 Dycus et al.
2007/0265616 A1 11/2007 Couture et al.
2008/0004616 A1 1/2008 Patrick
2008/0009860 A1 1/2008 Odom
2008/0015575 A1 1/2008 Odom et al.
2008/0021450 A1 1/2008 Couture
2008/0033428 A1 2/2008 Artale et al.
2008/0039835 A1 2/2008 Johnson et al.
2008/0039836 A1 2/2008 Odom et al.
2008/0045947 A1 2/2008 Johnson et al.
2008/0058802 A1 3/2008 Couture et al.
2008/0082100 A1 4/2008 Orton et al.
2008/0091189 A1 4/2008 Carlton
2008/0195093 A1 8/2008 Couture et al.
2008/0215051 A1 9/2008 Buysse et al.
2008/0243120 A1 10/2008 Lawes et al.
2008/0249527 A1 10/2008 Couture
2008/0312653 A1 12/2008 Arts et al.
2008/0319442 A1 12/2008 Unger et al.
2009/0012520 A1 1/2009 Hixson et al.
2009/0018535 A1 1/2009 Schechter et al.
2009/0024126 A1 1/2009 Artale et al.
2009/0043304 A1 2/2009 Tetzlaff et al.
2009/0048596 A1 2/2009 Shields et al.
2009/0062794 A1 3/2009 Buysse et al.
2009/0082766 A1 3/2009 Unger et al.
2009/0082767 A1 3/2009 Unger et al.
2009/0082769 A1 3/2009 Unger et al.
2009/0088738 A1 4/2009 Guerra et al.
2009/0088739 A1 4/2009 Hushka et al.

(56) References Cited

U.S. PATENT DOCUMENTS

| | | | |
|---|---|---|---|
| 2009/0088740 | A1 | 4/2009 | Guerra et al. |
| 2009/0088741 | A1 | 4/2009 | Hushka et al. |
| 2009/0088744 | A1 | 4/2009 | Townsend |
| 2009/0088745 | A1 | 4/2009 | Hushka et al. |
| 2009/0088746 | A1 | 4/2009 | Hushka et al. |
| 2009/0088747 | A1 | 4/2009 | Hushka et al. |
| 2009/0088748 | A1 | 4/2009 | Guerra et al. |
| 2009/0088749 | A1 | 4/2009 | Hushka et al. |
| 2009/0088750 | A1 | 4/2009 | Hushka et al. |
| 2009/0112206 | A1 | 4/2009 | Dumbauld et al. |
| 2009/0131934 | A1 | 5/2009 | Odom et al. |
| 2009/0149853 | A1 | 6/2009 | Shields et al. |
| 2009/0149854 | A1 | 6/2009 | Cunningham et al. |
| 2009/0171350 | A1 | 7/2009 | Dycus et al. |
| 2009/0171353 | A1 | 7/2009 | Johnson et al. |
| 2009/0182327 | A1 | 7/2009 | Unger |
| 2009/0187188 | A1 | 7/2009 | Guerra et al. |
| 2009/0198233 | A1 | 8/2009 | Chojin |
| 2009/0209957 | A1 | 8/2009 | Schmaltz et al. |
| 2009/0209960 | A1 | 8/2009 | Chojin |
| 2009/0234354 | A1 | 9/2009 | Johnson et al. |
| 2009/0248021 | A1 | 10/2009 | McKenna |
| 2010/0016857 | A1 | 1/2010 | McKenna et al. |
| 2010/0036375 | A1 | 2/2010 | Regadas |
| 2010/0042143 | A1 | 2/2010 | Cunningham |
| 2010/0049187 | A1 | 2/2010 | Carlton et al. |
| 2010/0057081 | A1 | 3/2010 | Hanna |
| 2010/0057082 | A1 | 3/2010 | Hanna |
| 2010/0057083 | A1 | 3/2010 | Hanna |
| 2010/0057084 | A1 | 3/2010 | Hanna |
| 2010/0063500 | A1 | 3/2010 | Muszala |
| 2010/0069903 | A1 | 3/2010 | Allen, IV et al. |
| 2010/0069904 | A1 | 3/2010 | Cunningham |
| 2010/0069953 | A1 | 3/2010 | Cunningham et al. |
| 2010/0076427 | A1 | 3/2010 | Heard |
| 2010/0076430 | A1 | 3/2010 | Romero |
| 2010/0076431 | A1 | 3/2010 | Allen, IV |
| 2010/0076432 | A1 | 3/2010 | Horner |
| 2010/0087816 | A1 | 4/2010 | Roy |
| 2010/0094287 | A1 | 4/2010 | Cunningham et al. |
| 2010/0100122 | A1 | 4/2010 | Hinton |
| 2010/0179545 | A1 | 7/2010 | Twomey et al. |
| 2010/0179546 | A1 | 7/2010 | Cunningham |

FOREIGN PATENT DOCUMENTS

| | | | |
|---|---|---|---|
| DE | 2415263 | | 10/1975 |
| DE | 2415263 | A1 | 10/1975 |
| DE | 2514501 | | 10/1976 |
| DE | 02514501 | A1 | 10/1976 |
| DE | 2627679 | | 1/1977 |
| DE | 2627679 | A1 | 1/1977 |
| DE | 3612646 | | 4/1987 |
| DE | 03612646 | A1 | 4/1987 |
| DE | 8712328 | U1 | 2/1988 |
| DE | 8712328 | | 3/1988 |
| DE | 4303882 | | 8/1994 |
| DE | 04303882 | C2 | 2/1995 |
| DE | 4403252 | | 8/1995 |
| DE | 04403252 | A1 | 8/1995 |
| DE | 19515914 | | 7/1996 |
| DE | 19515914 | C1 | 7/1996 |
| DE | 29616210 | U1 | 11/1996 |
| DE | 29616210 | | 1/1997 |
| DE | 19608716 | | 4/1997 |
| DE | 19608716 | C1 | 4/1997 |
| DE | 19751106 | | 5/1998 |
| DE | 19751106 | A1 | 5/1998 |
| DE | 19751108 | | 5/1999 |
| DE | 19751108 | A1 | 5/1999 |
| DE | 19738457 | | 1/2009 |
| DE | 19738457 | B4 | 1/2009 |
| EP | 0364216 | | 4/1990 |
| EP | 0467501 | | 1/1992 |
| EP | 0467501 | A1 | 1/1992 |
| EP | 0518230 | | 12/1992 |
| EP | 0541930 | | 5/1993 |
| EP | 0572131 | | 12/1993 |
| EP | 0572131 | A1 | 12/1993 |
| EP | 0584787 | | 3/1994 |
| EP | 0584787 | A1 | 3/1994 |
| EP | 0589453 | | 3/1994 |
| EP | 0589555 | | 3/1994 |
| EP | 0589555 | A1 | 3/1994 |
| EP | 0589453 | A3 | 4/1994 |
| EP | 0623316 | | 11/1994 |
| EP | 0624348 | | 11/1994 |
| EP | 0650701 | | 5/1995 |
| EP | 0624348 | A3 | 6/1995 |
| EP | 0364216 | B1 | 1/1996 |
| EP | 0694290 | | 3/1996 |
| EP | 0518230 | B1 | 5/1996 |
| EP | 0717966 | | 6/1996 |
| EP | 0754437 | | 3/1997 |
| EP | 0517243 | | 9/1997 |
| EP | 0517243 | B1 | 9/1997 |
| EP | 0541930 | B1 | 3/1998 |
| EP | 0853922 | | 7/1998 |
| EP | 0875209 | | 11/1998 |
| EP | 0878169 | | 11/1998 |
| EP | 0878169 | A1 | 11/1998 |
| EP | 0887046 | | 1/1999 |
| EP | 0623316 | B1 | 3/1999 |
| EP | 0650701 | B1 | 3/1999 |
| EP | 0923907 | | 6/1999 |
| EP | 0923907 | A1 | 6/1999 |
| EP | 0986990 | | 3/2000 |
| EP | 0986990 | A1 | 3/2000 |
| EP | 1034747 | | 9/2000 |
| EP | 1034747 | A1 | 9/2000 |
| EP | 1034748 | | 9/2000 |
| EP | 1025807 | | 10/2000 |
| EP | 1034746 | | 10/2000 |
| EP | 0694290 | B1 | 11/2000 |
| EP | 1050278 | | 11/2000 |
| EP | 1053719 | | 11/2000 |
| EP | 1053720 | | 11/2000 |
| EP | 1055399 | | 11/2000 |
| EP | 1055400 | | 11/2000 |
| EP | 1080694 | | 3/2001 |
| EP | 1082944 | | 3/2001 |
| EP | 1159926 | | 12/2001 |
| EP | 1177771 | | 2/2002 |
| EP | 1159926 | A3 | 3/2003 |
| EP | 0717966 | B1 | 4/2003 |
| EP | 1301135 | | 4/2003 |
| EP | 0887046 | B1 | 7/2003 |
| EP | 1330991 | | 7/2003 |
| EP | 1330991 | A1 | 7/2003 |
| EP | 1486177 | | 6/2004 |
| EP | 1472984 | | 11/2004 |
| EP | 0754437 | B2 | 12/2004 |
| EP | 1025807 | B1 | 12/2004 |
| EP | 0774232 | | 1/2005 |
| EP | 0774232 | B1 | 1/2005 |
| EP | 0853922 | B1 | 2/2005 |
| EP | 1527747 | | 5/2005 |
| EP | 1530952 | | 5/2005 |
| EP | 1530952 | A1 | 5/2005 |
| EP | 1532932 | | 5/2005 |
| EP | 1535581 | | 6/2005 |
| EP | 1609430 | | 12/2005 |
| EP | 1034746 | B1 | 3/2006 |
| EP | 1632192 | | 3/2006 |
| EP | 1642543 | | 4/2006 |
| EP | 1645238 | | 4/2006 |
| EP | 1645238 | A1 | 4/2006 |
| EP | 1645240 | | 4/2006 |
| EP | 1649821 | | 4/2006 |
| EP | 0875209 | B1 | 5/2006 |
| EP | 1707143 | | 10/2006 |
| EP | 1707143 | A1 | 10/2006 |
| EP | 1769765 | | 4/2007 |
| EP | 1769765 | A1 | 4/2007 |

(56) References Cited

FOREIGN PATENT DOCUMENTS

| | | | |
|---|---|---|---|
| EP | 1769766 | | 4/2007 |
| EP | 1929970 | | 6/2008 |
| EP | 1683496 | | 12/2008 |
| GB | 623316 | | 5/1949 |
| GB | 1490585 | | 11/1977 |
| GB | 2214430 | A | 6/1989 |
| GB | 2213416 | A | 8/1989 |
| GB | 2214430 | A | 9/1989 |
| JP | 61-501068 | | 9/1984 |
| JP | 501068 | | 9/1984 |
| JP | 6-502328 | | 3/1992 |
| JP | 502328 | | 3/1992 |
| JP | 5-5106 | | 1/1993 |
| JP | 05-40112 | | 2/1993 |
| JP | 06343644 | | 12/1994 |
| JP | 06343644 | A | 12/1994 |
| JP | 07265328 | | 10/1995 |
| JP | 07265328 | A | 10/1995 |
| JP | 08056955 | | 3/1996 |
| JP | 08056955 | A | 3/1996 |
| JP | 08252263 | | 10/1996 |
| JP | 08252263 | A | 10/1996 |
| JP | 09010223 | | 1/1997 |
| JP | 09010223 | A | 1/1997 |
| JP | 11244298 | | 9/1999 |
| JP | 11244298 | A | 9/1999 |
| JP | 2000-350732 | | 12/2000 |
| JP | 2000342599 | | 12/2000 |
| JP | 2000342599 | A | 12/2000 |
| JP | 2000350732 | A | 12/2000 |
| JP | 2001-008944 | | 1/2001 |
| JP | 2001008944 | A | 1/2001 |
| JP | 2001-029356 | | 2/2001 |
| JP | 2001029356 | A | 2/2001 |
| JP | 20011029356 | | 2/2001 |
| JP | 2001-128990 | | 5/2001 |
| JP | 2001128990 | A | 5/2001 |
| SU | 401367 | A1 | 10/1973 |
| SU | 401367 | | 11/1974 |
| WO | 89/00757 | | 1/1989 |
| WO | 92/04873 | | 4/1992 |
| WO | 92/06642 | | 4/1992 |
| WO | 93/21845 | | 11/1993 |
| WO | 94/08524 | | 4/1994 |
| WO | 94/20025 | | 9/1994 |
| WO | 95/02369 | | 1/1995 |
| WO | 95/07662 | | 3/1995 |
| WO | 95/15124 | | 6/1995 |
| WO | 96/05776 | | 2/1996 |
| WO | 96-22056 | A1 | 7/1996 |
| WO | WO 96/22056 | | 7/1996 |
| WO | 96/13218 | | 9/1996 |
| WO | 97/00646 | | 1/1997 |
| WO | 97/00647 | | 1/1997 |
| WO | 97/10764 | | 3/1997 |
| WO | 97/24073 | | 7/1997 |
| WO | 97/24993 | | 7/1997 |
| WO | 98/27880 | | 7/1998 |
| WO | 99/03407 | | 1/1999 |
| WO | 99/03408 | | 1/1999 |
| WO | 99/03409 | | 1/1999 |
| WO | 99/12488 | | 3/1999 |
| WO | 99-23933 | A2 | 5/1999 |
| WO | WO 99/23933 | | 5/1999 |
| WO | 99/40857 | | 8/1999 |
| WO | 99/40861 | | 8/1999 |
| WO | 99/51158 | | 10/1999 |
| WO | 99/66850 | | 12/1999 |
| WO | 00/24330 | | 5/2000 |
| WO | 00/24331 | | 5/2000 |
| WO | 0036986 | A1 | 6/2000 |
| WO | WO 00/36986 | | 6/2000 |
| WO | 00/41638 | | 7/2000 |
| WO | 00/47124 | | 8/2000 |
| WO | 00/53112 | | 9/2000 |
| WO | 01/17448 | | 3/2001 |
| WO | 0154604 | A1 | 8/2001 |
| WO | WO 01/54604 | | 8/2001 |
| WO | 02/07627 | | 1/2002 |
| WO | 02/067798 | | 9/2002 |
| WO | 02/080783 | | 10/2002 |
| WO | 02/080784 | | 10/2002 |
| WO | 02/080785 | | 10/2002 |
| WO | 02/080786 | | 10/2002 |
| WO | 02/080793 | | 10/2002 |
| WO | 02/080794 | | 10/2002 |
| WO | 02/080795 | | 10/2002 |
| WO | 02/080796 | | 10/2002 |
| WO | 02/080797 | | 10/2002 |
| WO | 02/080798 | | 10/2002 |
| WO | 02/080799 | A1 | 10/2002 |
| WO | 02/081170 | | 10/2002 |
| WO | 03/101311 | | 12/2003 |
| WO | 03/090630 | A3 | 4/2004 |
| WO | 2004/032776 | A1 | 4/2004 |
| WO | 2004/032777 | A1 | 4/2004 |
| WO | 2004/052221 | A1 | 6/2004 |
| WO | 2004/073488 | A2 | 9/2004 |
| WO | 2004/073490 | A2 | 9/2004 |
| WO | 2004/073753 | A2 | 9/2004 |
| WO | 2004/082495 | A1 | 9/2004 |
| WO | 2004/098383 | A2 | 11/2004 |
| WO | 2004/103156 | A2 | 12/2004 |
| WO | 2005/004734 | A1 | 1/2005 |
| WO | 2005/004735 | A1 | 1/2005 |
| WO | 2005/110264 | A2 | 11/2005 |

OTHER PUBLICATIONS

International Search Report EP 98958575.7 dated Sep. 20, 2002.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05021779.3 dated Jan. 18, 2006.
Int'l Search Report EP 05021197.8 dated Jan. 31, 2006.
Int'l Search Report—extended—EP 05021937.7 dated Mar. 6, 2006.
Int'l Search Report EP 05021780.1 dated Feb. 9, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
PCT/US01/11340 International Search Report dated Jun. 4, 2001.
PCT/US02/01890 International Search Report dated Jan. 22, 2002.
PCT/US02/11100 International Search Report dated Jul. 9, 2002.
PCT/USO4/03436 International Search Report dated Feb. 6, 2004.
PCT/US04/13273 International Search Report dated Apr. 29, 2004.
PCT/USO4/15311 International Search Report dated May 14, 2004.
EP 98944778 International Search Report dated Nov. 7, 2000.
EP 98958575 International Search Report dated Oct. 29, 2002.
EP 04027479 International Search Report dated Mar. 17, 2005.
EP 04027705 International Search Report dated Feb. 10, 2005.
EP 04027314 International Search Report dated Mar. 31, 2005.
PCT/US01/11218 International Search Report dated Apr. 6, 2001.
PCT/US99/24869 International Search Report dated Oct. 22, 1999.
PCT/US98/18640 International Search Report dated Sep. 8, 1998.
PCT/US98/23950 International Search Report dated Nov. 11, 1998.
McLellan et al. "Vessel Sealing for Hemostasis During Pelvic Surgery", 1999.
"Reducing Needlestick Injuries in the Operating Room", 2001.
McLellan et al. "Vessel Sealing for Hemostasis During Gynecologic Surgery", 1999.
E. David Crawford "Use of a Novel Vessel Sealing Technology in Management of the Dorsal Veinous Complex", 2000.
E. David Crawford "Evaluation of a New Vessel Sealing Device in Urologic Cancer Surgery", 2000.
Int'l Search Report EP 06 024122.1 dated Mar. 19, 2007.
Int'l Serach Report EP 07 001480.8 dated Apr. 12, 2007.

(56) References Cited

OTHER PUBLICATIONS

Int'l Search Report EP 07 001488.1 dated May 29, 2007.
Int'l Search Report—Extended EP 07 009029.5 dated Jul. 12, 2007.
Int'l Search Report EP 06 020574.7 dated Sep. 21, 2007.
Int'l Search Report EP 07 009026.1 dated Sep. 12, 2007.
Int'l Search Report EP 07 020283.3 dated Jan. 16, 2008.
Johnson et al. "Evaluation of a Bipolar Electrothermal Vessel Sealing Davice in Hemorrhoidectomy" Sales/Product Literature; Jan. 2004.
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Paul G. Horgan, "A Novel Technique for Parenchymal Division During Hepatectomy" The American Journal of Surgery, vol. 181, No. 3, .quadrature.Apr. 2001 pp. 236-237.
Carus et al., "Initial Experience With The LigaSure Vessel Sealing System in Abdominal Surgery" Innovations That Work,.quadrature. Jun. 2002.
LigaSure Vessel Sealing System, the Seal of Confidence in General, Gynecologic, Urologic, and Laparaoscopic Surgery Sales/Product Literature; Jan. 2004.
International Search Report PCT/US01/11224 dated Nov. 13, 2001.
Examiner's Report issued in Australia in Application No. 2009201853 dated Aug. 26, 2011.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques". OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.

(56) References Cited

OTHER PUBLICATIONS

Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Intl Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

TISSUE SEALER WITH NON-CONDUCTIVE VARIABLE STOP MEMBERS AND METHOD OF SEALING TISSUE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

The present application is a continuation application of U.S. Ser. No. 10/846,262 now U.S. Pat. No. 7,491,201 filed by Shields et al. on May 14, 2004, which claims the benefit of priority to U.S. Provisional Application Ser. No. 60/470,632 filed on May 15, 2003 by Shields et al., both of which are incorporated by reference herein.

BACKGROUND

The present disclosure relates to an electrosurgical instrument and method for performing electrosurgical procedures. More particularly, the present disclosure relates to an open or endoscopic bipolar electrosurgical forceps and method of using same which includes a selectively-variable, non-conductive stop member associated with one or both of the opposing jaw members. The selectively-variable, non-conductive stop member is designed to control the gap distance between opposing jaw members and enhance the manipulation and gripping of tissue during the sealing process.

TECHNICAL FIELD

Forceps utilize mechanical action to constrict, grasp, dissect and/or clamp tissue. Electrosurgical forceps utilize both mechanical clamping action and electrical energy to effect hemostasis by heating the tissue and blood vessels. By controlling the intensity, frequency and duration of the electrosurgical energy applied through the jaw members to the tissue, the surgeon can coagulate, cauterize and/or seal tissue.

In order to effect a proper seal with larger vessels or thick tissue, two predominant mechanical parameters must be accurately controlled: the pressure applied to the tissue; and the gap distance between the electrodes. As can be appreciated, both of these parameters are affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that fused tissue is optimum between about 0.001 inches to about 0.006 inches for small vessels and tissues and about 0.004 inches to about 0.008 inches for large, soft tissue structures. Below these ranges, the seal may shred or tear and above this range the tissue may not be properly or effectively sealed.

It is thought that the process of coagulating or cauterizing small vessels is fundamentally different than electrosurgical vessel or tissue sealing. "Vessel sealing" or "tissue sealing" is defined as the process of liquefying the collagen, elastin and ground substances in the tissue so that it reforms into a fused mass with significantly-reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them, however, larger vessels or tissue need to be "sealed" to assure permanent closure.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue which, if used for sealing purposes, would result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cauterizing, and cutting vessels or tissue.

Many of these instruments include blade members or shearing members which simply cut tissue in a mechanical and/or electromechanical manner and are relatively ineffective for vessel or tissue sealing purposes. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Thus, a need exists to develop an electrosurgical instrument which effectively and consistently seals tissue and solves the aforementioned problems. This instrument should be designed to regulate the gap distances between opposing jaws members to procure a consistent and effective seal. The instrument may also be designed to reduce the chances of the opposing jaws short circuiting during activation and assist in manipulating, gripping and holding the tissue prior to and during electrosurgical activation.

SUMMARY

According to one embodiment of the present disclosure, a bipolar forceps for sealing tissue is disclosed. The forceps includes an elongated shaft having opposing jaw members at a distal end thereof each of the jaw members including an electrically conductive sealing surface affixed thereto. The jaw members are movable relative to one another from a first position wherein the electrically conductive sealing surfaces are disposed in spaced relation relative to one another to a second position wherein the electrically conductive sealing surfaces are moved closer to one another for grasping tissue and maintained at a distance relative to one another. Each electrically conductive sealing surface is adapted to be connected to a source of electrical energy such that the electrically conductive sealing surfaces are capable of conducting energy through tissue grasped therebetween to effect a tissue seal. The distance between the electrically conductive sealing surfaces is selectively adjustable based upon a sensed pre-surgical condition during activation.

A method of sealing tissue is also contemplated by the present disclosure. The method includes an initial step of providing a bipolar forceps including a shaft having opposing jaw members at a distal end thereof which cooperate to grasp tissue therebetween, each of the jaw members including an electrically conductive sealing surface connected to a source of electrosurgical energy. The method also includes the steps of: adjusting a distance between the electrically conductive sealing surface based upon a sensed pre-surgical condition during activation, actuating the jaw members to grasp tissue between opposing jaw members, and conducting energy to the jaw members through tissue held therebetween to effect a tissue seal.

Another method of sealing tissue is also contemplated by the present disclosure. The method includes an initial step of providing a bipolar forceps including a shaft having opposing jaw members at a distal end thereof which cooperate to grasp tissue therebetween, each of the jaw members including an electrically conductive sealing surface connected to a source of electrosurgical energy. The method also includes the steps of actuating the jaw members to grasp tissue between opposing jaw members, conducting energy to the jaw members through tissue held therebetween to effect a tissue seal and adjusting a distance between the electrically conductive sealing surface based upon a sensed surgical condition during activation.

A further method of sealing tissue is contemplated by the present disclosure. The method includes an initial step of providing a bipolar forceps which includes a shaft having opposing jaw members at a distal end thereof each of the jaw members including an electrically conductive sealing surface, at least one of the electrically conductive sealing surfaces connected to a source of electrosurgical energy. The method also includes the steps of: actuating the jaw members to grasp tissue between opposing jaw members, wherein the jaw members are disposed at a distance relative to one another, adjusting the distance between the jaw members during the conducting step based upon a sensed surgical condition during activation and conducting energy to the jaw members through tissue held therebetween.

BRIEF DESCRIPTION OF THE DRAWINGS

Various embodiments of the present disclosure are described herein with reference to the drawings wherein.

DETAILED DESCRIPTION

Figure 1A:
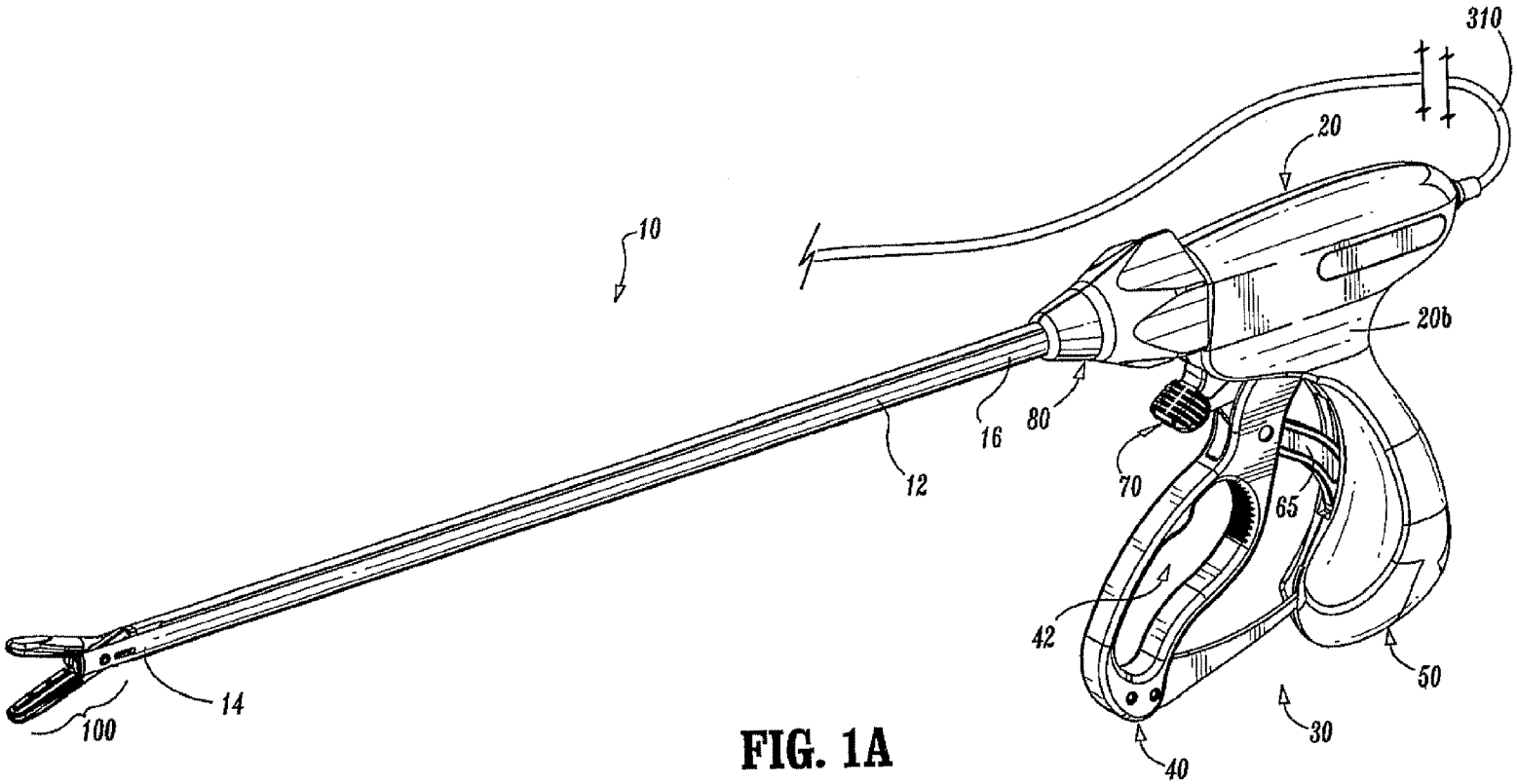
FIG. 1A is a perspective view of an endoscopic bipolar forceps which is configured to support a variable stop member assembly according to the present disclosure.

Referring now to FIGS. 1A-4, an endoscopic bipolar forceps 10 is shown by way of example for use with various endoscopic surgical procedures. Either an endoscopic instrument or an open instrument may be utilized for supporting the variable stop member assembly according to the present disclosure. Obviously, different electrical and mechanical connections and considerations apply to each particular type of instrument, however, the novel aspects with respect to the stop member assembly and its operating characteristics remain generally consistent with respect to both the open or endoscopic designs. Forceps 10 is shown by way of example and other electrosurgical forceps are also envisioned which may support the stop member assembly of the present disclosure. In the drawings and in the description which follows, the term "proximal", as is traditional, will refer to the end of the forceps 10 which is closer to the user, while the term "distal" will refer to the end of the forceps which is further from the user.

Figure 1B:
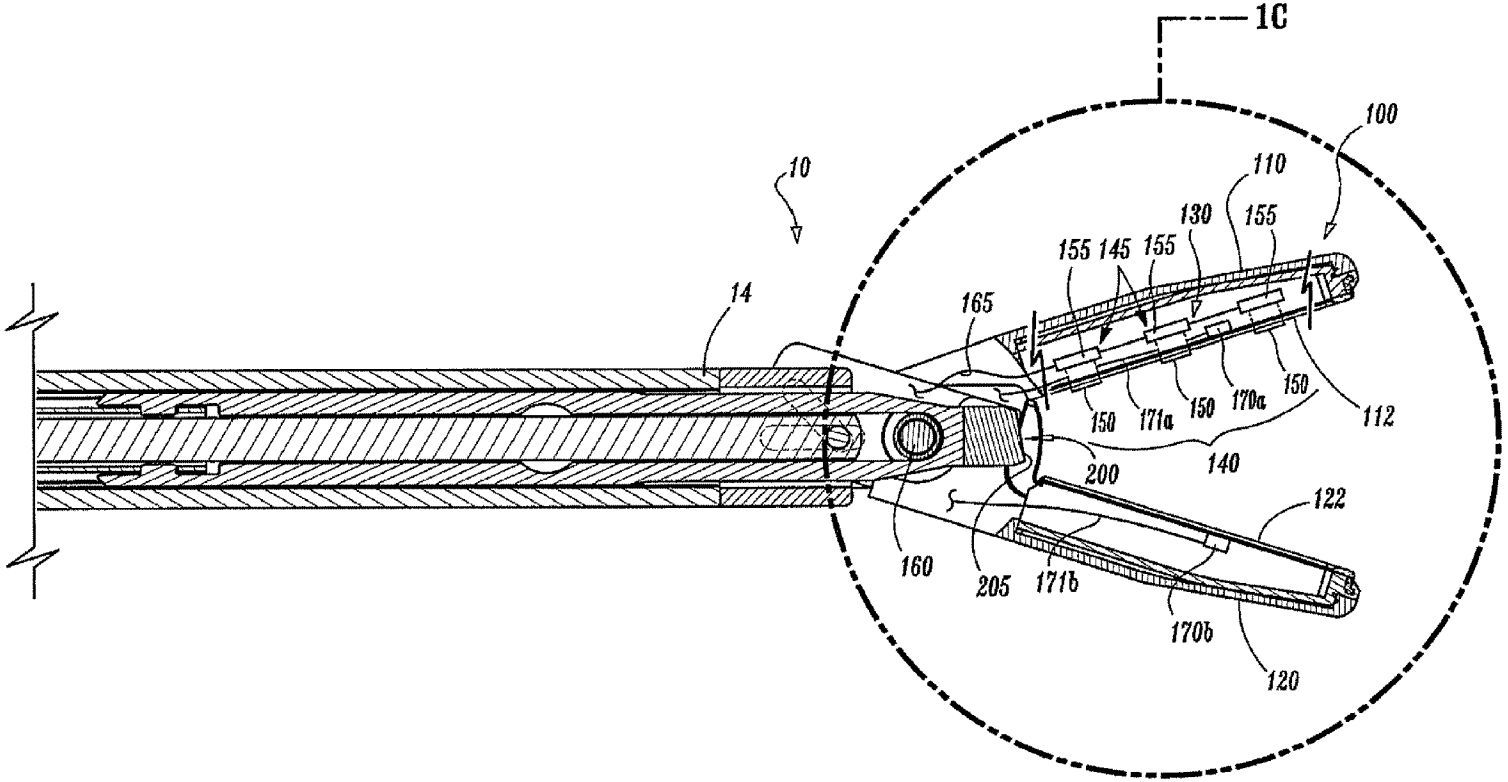
FIG. 1B is a side, partial internal view of an endoscopic forceps showing a selectively adjustable stop member assembly according to the present disclosure.
Figure 1C:
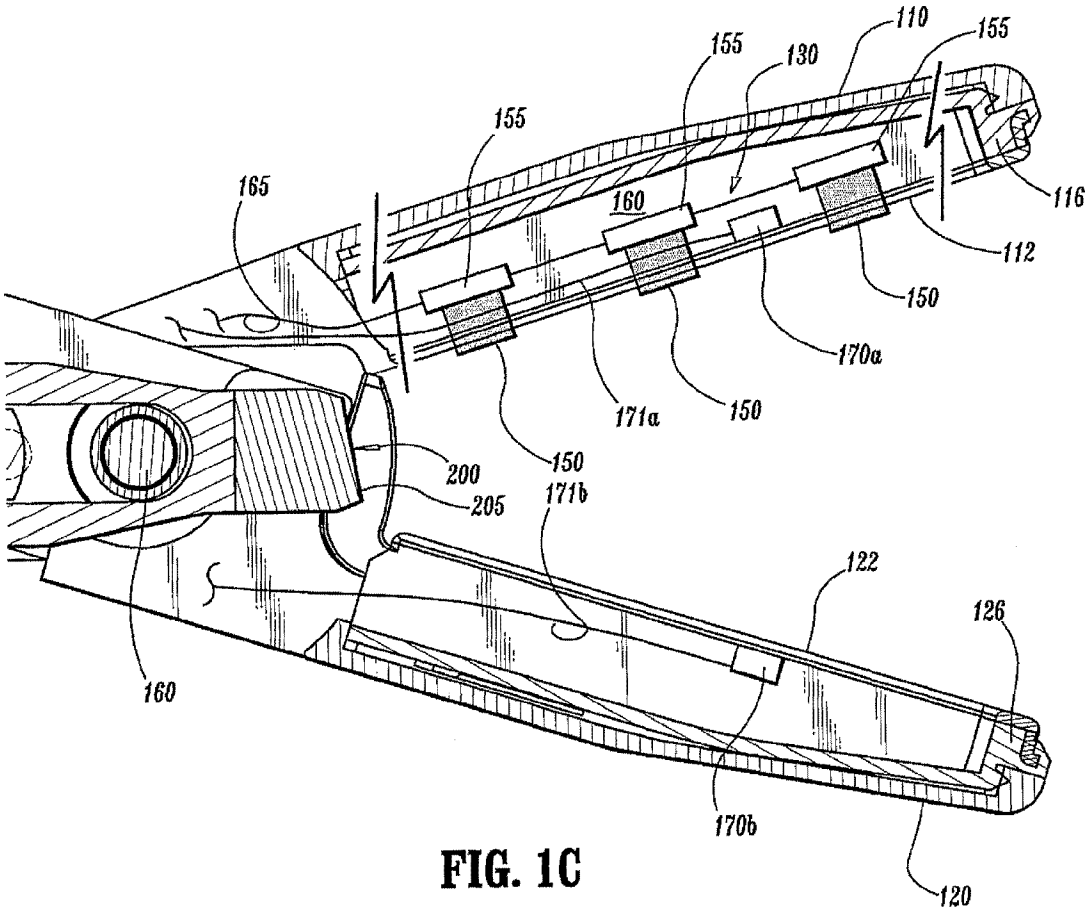
FIG. 1C is an enlarged view of the area of detail of FIG. 1B.

FIGS. 1A-1C show an endoscopic vessel sealing forceps 10 which is configured to support an electrode sealing assembly 100. More particularly, forceps 10 generally includes a housing 20, a handle assembly 30, a rotating assembly 80, a trigger assembly 70 and the end effector assembly 100 which mutually cooperate to grasp, seal and, if warranted, divide tissue. The forceps 10 includes a shaft 12 which has a distal end 14 dimensioned to mechanically engage the end effector assembly 100 and a proximal end 16 which mechanically engages the housing 20 proximate the rotating assembly 80.

Forceps 10 also includes a plug (not shown) which connects the forceps 10 to a source of electrosurgical energy, e.g., an electrosurgical generator 500, via an electrical cable 310. Handle assembly 30 includes a fixed handle 50 and a movable handle 40. Handle 40 moves relative to fixed handle 50 to actuate the end effector assembly 100 and enable a user to grasp and manipulate tissue 400 (See FIG. 3). The end effector assembly 100 includes a pair of opposing jaw members 110 and 120 which each have an electrically conductive sealing surface 112 and 122, respectively, attached thereto for conducting electrosurgical energy through tissue 400 held therebetween. More particularly, the jaw members 110 and 120 move in response to movement of the handle 40 from an open position wherein the electrically conductive sealing surfaces 112 and 122 are disposed in spaced relation relative to one another, to a clamping or closed position wherein the electrically conductive sealing surfaces 112 and 122 cooperate to grasp tissue therebetween.

The housing 20 encloses a drive assembly (not shown) which cooperates with the movable handle 40 to impart movement of the jaw members 110 and 120 from the open position to the clamping or closed position. One Example of a handle assembly is shown and described in commonly-owned U.S. application Ser. No. 10/389,894 entitled "VESSEL SEALER AND DIVIDER AND METHOD MANUFACTURING SAME" which is hereby incorporated by reference herein in its entirety. The handle assembly of this particular disclosure is generally be characterized as a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing surfaces 112 and 122 in a closed position against the tissue. The details relating to the inter-cooperative relationships of the inner-working components of forceps 10 are disclosed in the above-cited commonly-owned U.S. patent application Ser. No. 10/369,894. When the electrically conductive sealing surfaces 112 and 122 of the jaw members 110 and 120 are fully compressed about the tissue 400, the forceps 10 is now ready for selective application of electrosurgical energy (See FIG. 3). Another example of an endoscopic handle assembly is disclosed in U.S. patent application Ser. No. 10/460,926 entitled "VESSEL SEALER AND DIVIDER FOR USE WITH SMALL TROCARS AND CANNULAS", the entire contents of this application being incorporated by reference herein.

Experimental results suggest that the magnitude of pressure exerted on the tissue 400 by the electrically conductive sealing surfaces 112 and 122 is important in assuring a proper surgical seal. Pressures within a working range of about 3 $kg/cm^2$ to about 16 $kg/cm^2$ and, in embodiments, within a working range of about 7 $kg/cm^2$ to about 13 $kg/cm^2$ have been shown to be effective for sealing various small tissue types. Pressure within a working range of about 4.5 $kg/cm^2$ to about 8.5 $kg/cm^2$ are optimal for large soft tissue structures.

As explained above, movement of the handle assembly 30, e.g., via a four-bar linkage, ultimately causes the opposing jaw members 110 and 120 to move relative to one another. As can be appreciated, the significant mechanical advantage associated with the four-bar linkage permits facile, consistent and uniform compression of the jaw members 110 and 120 about the tissue 400. Other details and advantages of the four-bar mechanical linkage are more fully discussed with respect to the above-mentioned commonly-owned U.S. patent application Ser. No. 10/369,894.

As best seen in FIGS. 1A-1C, forceps 10 also includes a trigger 70 which advances a knife 200 disposed within the end effector assembly 100. Once a tissue seal is formed, the user can activate the trigger 70 to separate the tissue 400 along the tissue seal. Knife 200 includes a sharpened edge 205 for severing the tissue 400 held between the jaw members 110 and 120 at the tissue sealing site.

A rotating assembly 80 may also be incorporated with forceps 10. In embodiments, rotating assembly 80 is mechanically associated with the shaft 12 and the drive assembly (not shown). Movement of the rotating assembly 80 imparts similar rotational movement to the shaft 12 which, in turn, rotates the end effector assembly 100. These features along with the unique electrical configuration for the transference of electrosurgical energy through the handle assembly 20 and the rotating assembly 80 are described in more detail in the above-mentioned commonly-owned U.S. patent application Ser. Nos. 10/369,894 and 10/460,926.

Figure 2:
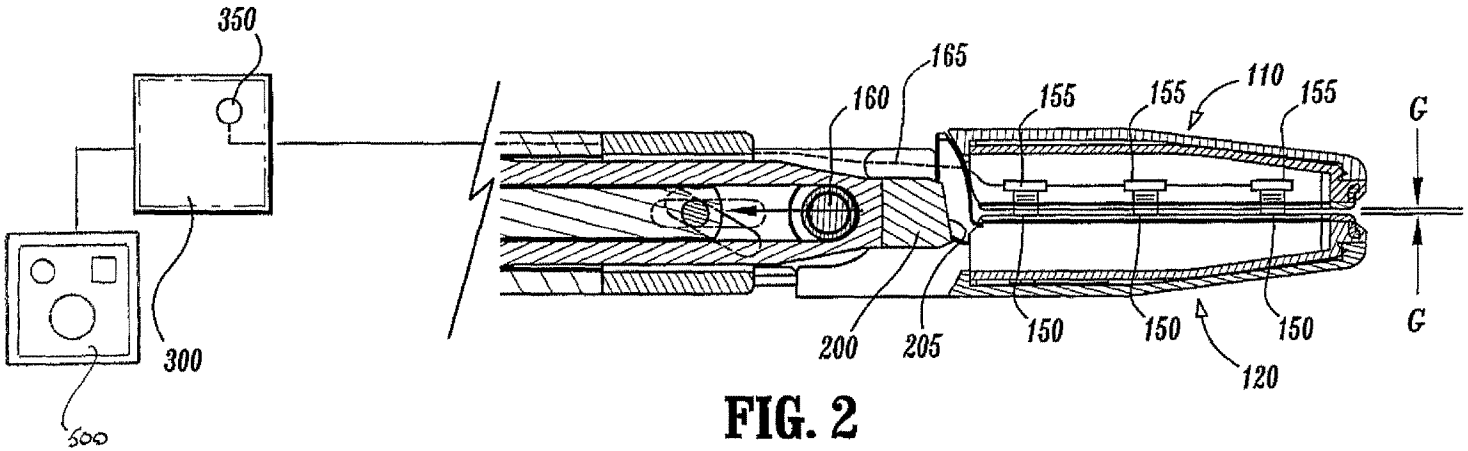
FIG. 2 is a side, partial internal view of an end effector assembly shown in closed configuration.
Figure 3:
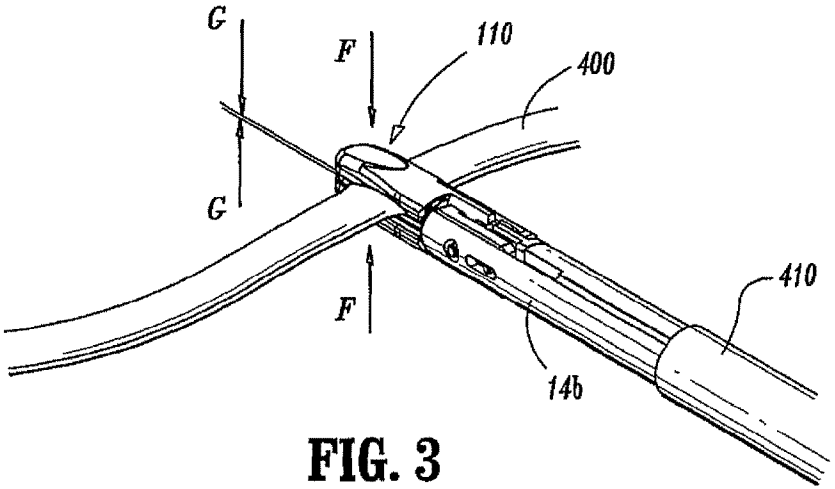
FIG. 3 is a rear, perspective view of the end effector of FIG. 2 shown with tissue grasped therein.

As best seen with respect to FIGS. 1A-2, end effector assembly 100 attaches to the distal end 14 of shaft 12. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed.

Each of the jaw members 110 and 120 includes an electrically conductive sealing surface 112 and 122, respectively disposed on an inner-facing surface thereof. It is envisioned that the electrically conductive surfaces 112 and 122 cooperate to seal tissue 400 held therebetween upon the application of electrosurgical energy. Insulators 116 and 126 (together with the outer, non-conductive surfaces of the jaw members 110 and 120) may be included to limit and/or reduce many of the known undesirable effects related to tissue sealing, e.g., flashover, thermal spread and stray current dissipation (See FIG. 1C).

In embodiments, a least one of the electrically conductive surfaces, e.g., 112, of one of the jaw members, e.g., 110, includes a longitudinally-oriented channel 210 defined therein (See FIG. 4) which extends from the proximal end of the electrically conductive sealing surface 112 to the distal end. The channel 210 facilitates longitudinal reciprocation of the knife 200 along a desired cutting plane to effectively and accurately separate the tissue 400 along a formed tissue seal.

By controlling the intensity, frequency and duration of the electrosurgical energy applied to the tissue 400, the user can selectively seal tissue 400. As mentioned above, two mechanical factors play an important role in determining the resulting thickness of the sealed tissue and effectiveness of the seal, i.e., the pressure applied between opposing jaw members 110 and 120 and the gap distance "G" between the opposing sealing surfaces 112 and 122 of the jaw members 110 and 120, respectively, during the sealing process.

However, thickness of the resulting tissue seal cannot be adequately controlled by force alone. In other words, too much force and the two jaw members 110 and 120 would touch and possibly short resulting in little energy traveling through the tissue 400 thus resulting in a bad tissue seal. Too little force and the seal would be too thick. Applying the correct force is also important for other reasons: to reduce the tissue impedance to a low enough value that allows enough current through the tissue 400; and to overcome the forces of expansion during tissue heating in addition to contributing towards creating the required end tissue thickness which is an indication of a good seal.

In order to achieve a desired spacing between the electrically conductive surfaces 112 and 122 of the respective jaw members 110 and 120, (i.e., gap distance "G") and apply a desired force to seal the tissue 400, at least one jaw member 110 and/or 120 includes at least one stop member, e.g., 150, to limit the movement of the two opposing jaw members 110 and 120 relative to one another. In one embodiment, the stop member, e.g., 150, extends from at least one of the sealing surfaces 112, 122 a predetermined distance according to the specific material properties of the stop member 150 (e.g., compressive strength, thermal expansion, etc.) to yield a consistent and accurate gap distance "G" during sealing. In one embodiment, the gap distance "G" between opposing sealing surfaces 112 and 122 during sealing ranges from about 0.001 inches to about 0.008 inches. For smaller tissue types the gap distance may be between about 0.002 inches to about 0.003 inches and for larger tissue types the gap distance may be between about 0.004 inches to about 0.007 inches.

In embodiments, stop members 150 are made from an insulative material, e.g., parylene, nylon and/or ceramic and are dimensioned to limit opposing movement of the electrically conductive sealing surfaces 112 and 122 to within the above mentioned gap range "G". It is envisioned that the stop members 150 may be disposed on one or both of the electrically conductive sealing surfaces 112 and 122 depending upon a particular purpose or to achieve a particular result.

As best shown in FIGS. 1B and 1C, at least of the jaw members includes a selectively adjustable stop member assembly 140 which allows a surgeon to regulate the gap distance "G" depending upon a particular tissue type and/or tissue thickness. More particularly, at least one of the jaw members, e.g., jaw member 110, includes a cavity 130 disposed therein which is dimensioned to house the stop member assembly 140. Stop member assembly 140 includes a plurality of selectively adjustable stop member control units 145 which includes a stop member 150 and a controller 155. More particularly, the controller 155 is designed to receive signals from a control source 300 (FIG. 2) which may be attached to an electrosurgical generator 500 or incorporated into the housing of the forceps 10. The control source 300 signals the controller 155 to electrically, mechanically or electro-mechanically adjust the distance the stop member(s) 150 projects or extends from the electrically conductive sealing surface 112 (and/or 122). The distance that the stop member(s) 150 projects from the electrically conductive sealing surface 112 (and/or 122) determines the ultimate gap distance "G" (See FIG. 2).

It is envisioned that the controller 155 may adjust the distance that each stop member 150 extends from the sealing surface 112 is any known fashion. For example, each stop member 150 and its corresponding controller 155 may be threadably connected such that the controller 155 "unscrews" the stop member 150 to adjust the distance that the stop member 150 extends from the sealing surface 112. Thus, by controlling the amount that the stop member 150 unscrews from the controller 155, a surgeon can selectively regulate (or a control source 300 may automatically regulate) the gap distance "G". Other mechanical systems (not shown) are also envisioned to allow selective regulation of the gap distance "G", e.g., gearing mechanisms, camming mechanisms, pneumatic mechanisms, hydraulic mechanisms, etc. Electromechanical systems are also contemplated, e.g., electro-mechanical actuators, ferroelectric actuators, piezo-electric actuators, piezo-ceramic actuators, magnetostrictors and rotational actuators, etc.

It is envisioned that the controller 155 may cooperate with a sensor assembly 170a and 170b (or a plurality of sensors) which determines or measures tissue thickness, tissue moisture, tissue type, tissue impedance, etc. and automatically signals the control source 300 to signal the controller 155 to adjust the stop members 150 to extend a specific distance (i.e., a "desired" gap distance "G") from the electrically conductive sealing surface 112 prior to activation. The desired gap distance "G" (which directly corresponds to the specified distance that the stop members 150 extend from the electrically conductive sealing surface 112) may be selected from a look-up table or determined by a computer algorithm stored within the control source 300. It is envisioned that the stop members are selectively adjustable to protrude about 0.001 inches to about 0.008 inches from the electrically conductive sealing surfaces 112 (and/or 122) of the jaw members 110 (and/or 120).

It is also contemplated that one or more stop members 150 may be individually controllable (via controller 155 or manually) to vary the gap distance along or across the sealing surfaces depending upon a particular purpose or to achieve a particular tissue seal. Moreover, it is envisioned that varying the distance that stop member(s) project from the sealing surface(s) may produce different results for different tissue types and may prove desirable for one or more particular tissue types or one or more different surgical procedures.

The sensors 170a and 170b are connected to the control source 300 (or electrosurgical generator) via cables 171a and 171b, respectively. The sensors 170a and 170b may form a part of a closed-loop control system which automatically adjusts the forceps 10 prior to and/or during activation based on pre-surgical parameters and continually-sensed parameters. For example, the stop members 150 may be adjusted based upon a pre-surgical parameter such as tissue thickness, tissue type, tissue compliance, tissue impedance, etc. One example of a closed-loop control system is described in commonly-owned U.S. patent application Ser. No. 10/427,832 filed on May 1, 2003 entitled "METHOD AND SYSTEM FOR CONTROLLING OUTPUT OF RF MEDICAL GENERATOR" the entire contents of which are hereby incorporated by reference herein. For example, the stop member(s) 150 may be set according to a pre-surgical condition (either automatically based upon a sensed condition (e.g., tissue impedance, tissue type, tissue clarity, tissue compliance, etc.)) or manually by the surgeon.

It is also envisioned that the stop member(s) 150 may be adjusted during activation based upon a continually-sensed surgical condition (e.g., tissue impedance, tissue type, tissue clarity, tissue compliance, etc.) utilizing a feed back control loop. It is envisioned that this may allow the control system to achieve a "slow close" condition. More particularly, one technique for sealing larger tissue structures (e.g., lung, liver, bronchus, etc.) is a so-called "slow-close" surgical technique which involves activating the surgical instrument prior to obtaining a fully ratcheted position. As can be appreciated, this type of procedure is very difficult to master manually due to the many variables involved with the sealing process and, as a result, the instrument may short or the sealing cycle may complete prior to obtaining the fully closed ratcheted position. It is envisioned that the automatic stop member adjustment system described above may enable slow close activation which may lead to more effective sealing of large tissue structures. For example, the surgeon can grasp the tissue in a customary manner and fully ratchet the forceps about the tissue within the desired pressure ranges. The stop member(s) 150 can be programmed to activate in a "slow close" manner and automatically adjust from a large gap distance e.g., about 0.10 inches to within a gap range of about 0.001 inches to about 0.008 inches during activation. The stop member control assembly 140 may also be coupled to a feedback control system which automatically regulates the "slow close" technique based upon tissue thickness, tissue temperature, tissue impedance, tissue moisture, tissue clarity, tissue compliance during activation. As can be appreciated, this enables any surgeon to perform a slow close technique for sealing lager tissue structures.

A control knob 350 (See FIG. 2) may also be included to permit a surgeon to manually adjust the distance that the stop members 150 protrude from the electrically conductive sealing surface 112 (and/or 122) depending upon a particular purpose.

Figure 4:
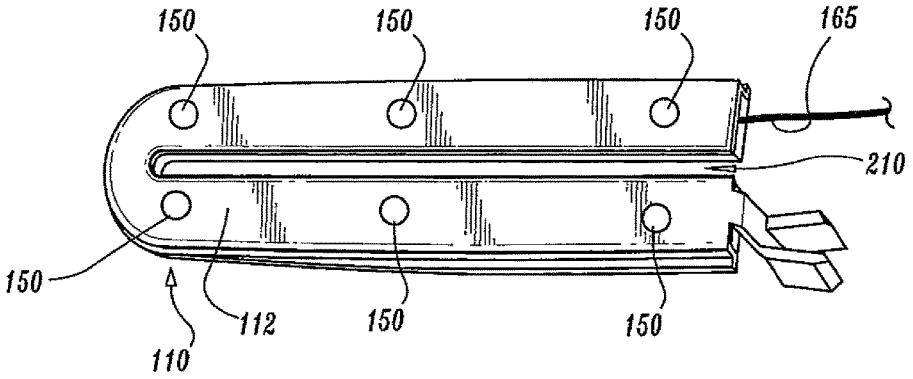
FIG. 4 is an enlarged, perspective view of an electrically conductive sealing surface of the end effector assembly showing a series of selectively adjustable stop members disposed thereon.

FIG. 4 shows one contemplated configuration of the stop members 150 disposed on or protruding from the electrically conductive sealing surface 112. It is envisioned that the stop members 150 can be positioned on either or both jaw members 110 and 120 depending upon a particular purpose or to achieve a desired result. More particularly and as illustrated in FIG. 4, a series of longitudinally-oriented tab-like stop members 150 are disposed along either side of the knife channel 210 of jaw member 110. In embodiments, the stop members 150 may be configured in any known geometric or polynomial configuration, e.g., triangular, rectilinear, circular, ovoid, scalloped, etc., depending upon a particular purpose. Moreover, it is contemplated that any combination of different stop members 150 may be assembled along the sealing surfaces 112 (and/or 122) to achieve a desired gap distance "G". A ceramic or insulative coating may be deposited or sprayed onto the tissue engaging surface of the stop members 150. Thermal spraying techniques are contemplated which involve depositing a broad range of heat resistant and insulative materials on the tissue engaging surfaces of the stop members 150, high velocity Oxy-fuel deposition, plasma deposition, etc.

Further, although it is the stop members 150 may be selectively adjustable to protrude about 0.001 inches to about 0.008 inches from the electrically conductive sealing surfaces 112, in some cases the stop members 150 may protrude more or less depending upon a particular purpose. For example, it is contemplated that the type of material used for the stop members 150 and that material's ability to absorb the desired range of compressive closure forces between jaw members 110 and 120 will vary and, therefore, the overall distance that the stop members 150 may have to extend from the electrically conducive sealing surfaces 112 may have to adjusted to compensate for the particular stop member 150 material being utilized to produce the desired gap distance "G".

In other words, the compressive strength of the stop member material along with the desired or ultimate gap distance "G" required for effective sealing are parameters which should be considered during activation since one material may have to be adjusted differently from another material to achieve the same gap distance "G". For example, the compressive strength of nylon is different from ceramic and, therefore, the nylon material may have to extend a greater distance from the electrically conductive sealing surface 112 to counteract the closing force of the opposing jaw members 110 and 120 and to achieve the same desired gap distance "G". As can be appreciated, these considerations may be automatically regulated or controlled at the control source 300 via a computer algorithm or look up table.

The present disclosure also relates to a method of sealing tissue utilizing a selectively adjustable stop member 150 and includes the steps of: providing a bipolar forceps 10 having a shaft 12 and opposing jaw members 110 and 120 which cooperate to grasp tissue 400 therebetween; at least one selectively extendible and non-conductive stop member 150 disposed on an electrically conductive surface 112 of at least one of the jaw members, e.g., 110, which regulates the distance between the jaw members 110 and 120 when tissue 400 is held therebetween. The method further includes the steps of: connecting the electrically conductive sealing surfaces 112 and 122 of the jaw members 110 and 120 to a source of electrosurgical energy; adjusting the distance that the stop members 150 extend from the electrically conductive sealing surface 112 depending upon a pre-surgical condition or parameter; actuating the jaw members 110 and 120 to grasp tissue 400 between opposing electrically conductive sealing surfaces 112 and 122; conducting energy to the electrically conductive sealing surfaces 112 and 122 through tissue 400 held therebetween to effect a seal.

The adjusting step of the method may further include the steps of: sensing a pre-surgical condition or parameter such as tissue type, tissue thickness, tissue compliance, tissue impedance, etc. and signaling the controller 155 (via the control source 300 or directly) to selectively extend or retract the stop members 150 relative to the electrically conductive sealing surface 112 depending upon the sensed pre-surgical condition or parameter.

At least one of the jaw members, e.g., 110, of the providing step includes may include an electrically conductive sealing surface 112 having a longitudinally-oriented channel 210 defined therein which facilitates actuation of a knife 200 in a longitudinally reciprocating fashion within the channel 210 for severing the tissue 400 proximate the tissue sealing site. As can be appreciated, the method may also include the step of severing the tissue 400 along the tissue seal.

From the foregoing and with reference to the various figure drawings, those skilled in the art will appreciate that certain modifications can also be made to the present disclosure without departing from the scope of the same. For example, it may be desirable to add other features to the forceps 10, e.g., an articulating assembly to axially displace the end effector assembly 100 relative to the elongated shaft 12.

Moreover, it is contemplated that the presently disclosed forceps may include a disposable end effector assembly 100 which is selectively engageable with at least one portion of the electrosurgical instrument, e.g., shaft 12 and/or handle assembly 80. In one embodiment, the electrically conductive sealing surfaces 112 and 122 of the jaw members 110 and 120 are relatively flat to avoid current concentrations at sharp edges and to avoid arcing between high points. In addition and due to the reaction force of the tissue 400 when engaged, jaw members 110 and 120 may be manufactured to resist bending. For example, the jaw members 110 and 120 may be tapered along their respective widths which is advantageous for two reasons: 1) the taper will apply constant pressure for a constant tissue thickness at parallel; 2) the thicker proximal portion of the jaw members 110 and 120 will resist bending due to the reaction force of the tissue 400.

It is also contemplated that one or more stop members may be disposed adjacent to one or both electrically conductive sealing surfaces to regulate the gap distance between conductive surfaces. Alternatively, one or more selectively extendible stop members may be disposed on one or both electrically conductive sealing surface(s) and one or more stop members may be disposed adjacent to at least one of the electrically conductive surfaces. As can be appreciated, both sets of selectively adjustable stop members would cooperate with the controller (or manually) to adjust and regulate the gap distance.

The stop member(s) may be dimensioned in any known geometric configuration and may be disposed on or adjacent to one or both of the electrically conductive tissue sealing surfaces or operatively associated with one or both jaw members. Moreover, the controller and stop member may be integrally associated with one another or may be formed from two or more components so long as the stop member is selectively adjustable to regulate the distance between the jaw members prior to and/or during electrical activation.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps for sealing tissue, comprising:

an elongated shaft having opposing jaw members at a distal end thereof, each of the jaw members including an electrically conductive sealing surface affixed thereto, at least one of the jaw members movable relative to the other jaw member from a first position wherein the electrically conductive sealing surfaces are disposed in spaced relation relative to one another to a second position wherein the electrically conductive sealing surfaces are moved closer to one another for grasping tissue[;], each electrically conductive sealing surface adapted to connect to a source of electrical energy such that the electrically conductive sealing surfaces are capable of conducting energy through tissue grasped therebetween to effect a tissue seal[, wherein]*; and*

*a stop member extending from one of the electrical conductive sealing surfaces, the stop member adjustable during activation to regulate* the distance between the electrically conductive sealing surfaces [is automatically adjustable] in response to a sensed pre-surgical condition during activation.

2. A bipolar forceps for sealing tissue according to claim 1, further including at least one controller engagable with at least one of the electrically conductive sealing surfaces, the controller configured to *adjust the stop member to* control the distance between the electrically conductive sealing surfaces in response to a signal from a control source.

3. A bipolar forceps for sealing tissue according to claim 2, wherein the bipolar forceps includes at least one sensor disposed on at least one of the jaw members, the at least one sensor configured to sense the sensed pre-surgical condition selected from the group consisting of tissue impedance, tissue thickness, tissue compliance, and tissue type, and further configured to relay the sensed information to a control source which, in turn, is configured to send a signal to the *at least one* controller.

4. A bipolar forceps for sealing tissue according to claim 1, wherein the forceps includes a selectively extendible knife for severing tissue along the tissue seal.

5. A bipolar forceps for sealing tissue according to claim 1, wherein the electrically conductive sealing surfaces are adjusted a distance in the range of about 0.001 inches to about 0.008 inches relative to one another.

6. A method of sealing tissue comprising [the steps of]*:* providing a bipolar forceps including a shaft having opposing jaw members at a distal end thereof which cooperate to grasp tissue therebetween, each of the jaw members including an electrically conductive sealing surface [connected] *affixed thereto and adapted to connect* to a source of electrosurgical energy;

[automatically adjusting a distance between the electrically conductive sealing surface in response to a sensed pre-surgical condition during activation;]

actuating the jaw members to grasp tissue between opposing jaw members; [and]

conducting energy to the jaw members through tissue grasped therebetween to effect a tissue seal*; and*

*adjusting a stop member extending from one of the electrically conductive sealing surfaces to regulate a distance between the electrically conductive sealing surfaces in response to a sensed pre-surgical condition while energy is conducted to the jaw members.*

7. A method of sealing tissue according to claim 6, wherein the adjusting [step] *the stop member* further includes [the steps of]*:* sensing the sensed pre-surgical condition; and signaling a controller to selectively adjust *the stop member such that* the distance between the electrically conductive sealing surfaces depending upon the sensed pre-surgical condition.

8. A method of sealing tissue according to claim 6, further comprising the step of severing the tissue along the tissue seal.

9. A method of sealing tissue according to claim 6, wherein after the conducting step, the method further includes the steps of:

sensing a tissue parameter during electrosurgical activation; and signaling a controller to selectively adjust *the stop member such that* the distance between the electrically conductive sealing surfaces *is* based upon the sensed tissue parameter.

10. A method of sealing tissue according to claim 9, wherein after the [sensed] signaling step, the method further includes the step of repeating the sensing and signaling steps until a desired seal is effected.

[11. A method of sealing tissue comprising the steps of:

providing a bipolar forceps including a shaft having opposing jaw members at a distal end thereof which cooperate to grasp tissue therebetween, each of the jaw members including an electrically conductive sealing surface connected to a source of electrosurgical energy;

actuating the jaw members to grasp tissue between opposing jaw members, wherein the jaw members are disposed at a distance relative to one another;

automatically adjusting the distance between the electrically conductive sealing surfaces in response to a sensed surgical condition during activation; and conducting energy to the jaw members through tissue grasped therebetween to effect a tissue seal.]

[12. A method of sealing tissue according to claim 11, wherein the adjusting step further includes the step of communicating with a feedback control system that continually senses surgical conditions during activation to automatically regulate the distance between the electrically conductive sealing surfaces.]

[13. A method of sealing tissue according to claim 11, wherein the adjusting step, further includes the step of communicating with a feedback control system to automatically regulate the distance between the electrically conductive sealing surfaces based upon at least one of tissue impedance, tissue temperature, tissue thickness, tissue moisture, tissue compliance or tissue clarity during activation.]

[14. A method of sealing tissue according to claim 11, wherein the step of adjusting includes adjusting the distance between the electrically conductive sealing surfaces so that the distance between the electrically conductive sealing surfaces becomes increasingly smaller.]

* * * * *